US006331536B1

(12) United States Patent
Radulovacki et al.

(10) Patent No.: US 6,331,536 B1
(45) Date of Patent: Dec. 18, 2001

(54) PHARMACOLOGICAL TREATMENT FOR SLEEP APNEA

(75) Inventors: Miodrag Radulovacki, Chicago; David W. Carley, Evanston, both of IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/622,823

(22) PCT Filed: Feb. 26, 1999

(86) PCT No.: PCT/US99/04347

§ 371 Date: Aug. 23, 2000

§ 102(e) Date: Aug. 23, 2000

(87) PCT Pub. No.: WO99/43319

PCT Pub. Date: Sep. 2, 1999

Related U.S. Application Data

(60) Provisional application No. 60/076,216, filed on Feb. 27, 1998.

(51) Int. Cl.[7] ..................... A61K 31/55; A61K 31/505; A61K 31/44; A61K 31/445

(52) U.S. Cl. ................. 514/214.02; 514/220; 514/259; 514/288; 514/299; 514/325

(58) Field of Search .............................. 514/214.02, 220, 514/259, 288, 299, 325

(56) References Cited

U.S. PATENT DOCUMENTS

| | | | |
|---|---|---|---|
| 5,075,290 | 12/1991 | Findley et al. | 514/46 |
| 5,082,665 | 1/1992 | Verny | 424/464 |
| 5,166,158 | 11/1992 | Zimmerman et al. | 514/269 |
| 5,356,934 | * 10/1994 | Robertson et al. | 514/649 |
| 5,612,379 | 3/1997 | Laurent | 514/618 |

FOREIGN PATENT DOCUMENTS

| | | |
|---|---|---|
| 0 442 423A1 | 8/1991 | (EP) . |
| 0 442 424A1 | 8/1991 | (EP) . |
| 0 518 767A2 | 12/1992 | (EP) . |
| WO 99/00119 | 1/1999 | (WO) . |
| WO 99/25356 | 5/1999 | (WO) . |

OTHER PUBLICATIONS

Armstrong et al., *J. Physiol. (Lond.)*, 365:104 P (1985).
Badr et al., "Treatment of Refractory Sleep Apnea with Supplemental Carbon Dioxide", *Am. J. Respir. Crit. Care Med.*, 150:561–564(1994).
Bennington et al., "Methodology: Scoring and Computerized Methods", *Sleep*, 17:28–36 (1994).
Bisgard et al., "Effects of Dopamine, Norepinepherine and 5–Hydroxytryptamine on the Carotid Body of the Dog", *Resp. Physiol.* 37:61–80 (1979).
Black et al., "Species Difference in Carotid Body Response of Cat and Dog To Dopamine and Seretonin", *Am. J. Physiol.*, 223:1097–1102 (1972).

Butler et al., "Pharmacological Properties of GR38032F, a Novel Anatagonist at 5–HT$_3$ Receptors," *Br. J. Pharmacol.*, 94:397–412 (1988).
Carley et al., "Sleep Apnea in Normal and REM Sleep–Deprived Normotensive Wistar–Kyoto and Spontaneously Hypertensive (SHR) Rats," *Physiol. Behav.*, 59:827–831 (1996).
Carley et al., "The Heart and Sleep: Hydralazine Reduces Elevated Sleep Apnea Index in Spontaneously Hypertensive (SHR) Rat to Equivalence With Normotensive Wistar–Kyoto Rats," *Sleep*, 19:363–366 (1996).
Christon et al., "Effects of Inspired Gas on Sleep–Related Apnea in the Rat," *J. Appl. Physiol.*, 80:2102–2107 (1996).
Coon, R.L., "Reflex Effects of Lung Inflammation on Tracheomotor Tone Observed During Apnea Produced By The Hering–Breuer Reflex", *J. Appl. Physiol.*, 76:2546–2551 (1994).
deBoer, Th., "The Pharmacologic Profile of Mirtazapine", *J. Clin. Psychiatr.*, 57(4):19–25 (1996).
Devane, C., "Differential Pharmacology of Newer Antidepressants", *J. Clin. Psychiatry.*, 59(20):85–93 (1998).
Douglas et al., "Effects of CPAP On Vigilance and Related Functions In Patients With the Sleep Apnea/Hypopnea Syndrome", *Sleep*, 23:S147–149(2000).
Downs et al., "The Effect of Antihistamines on the Laryngeal Chemoreflex", *Laryngoscope*, 105:857–861 (1995).
Goda et al., "The Role of 5–HT3 Receptor–Mediated Mechanisms on 5–HT–induced Apnea in Anesthetized Rats," *European J. Pharmacology*, 183/3:705–706 (1990).
Greulich et al., "Sleep Behavior in Patients with Parkinson's Disease," *Schlafverhalten Bei Patienten Mit Morbus Parkinson Somnologie*, 2:163–171 (1998).
Grogaard et al., "Effect of Beta–Adrenergic Agonists On Apnea Reflexes In Newborn Lambs", *Pediatr. Res.*, 17:213–219 (1983).
Hagan et al., "Effect of the 5–HT$_3$ Receptor Antagonist, GR38032F, On Responses To Injection of a Neurokinin Agonist into the Ventral Tegmental Area of the Rat Brain," *Eur. J. Pharmacol.*, 138:303–305 (1987).
Hanzel et al., "Response of Obstructive Sleep Apnes to Fluoxetine and Protriptyline", *Chest.*, 100:416–421 (1991).
Hilaire et al., "Changes in Serotoniin Metabloism May Elicit Obstructive Apnoea ib the Newnborn Rat", *J. Physiol.*, 466:367–382 (1993).
Hudgel et al., "Abnormal Serotonergic Stimulation of Cortisol Production in Obstructive Sleep Apnea," *Am. J. Respir. Crit. Care Med.*, 152:186–192 (1995).
Hudgel, "Pharmacologic Treatment of Obstructive Sleep Apnea," *J. Lab. Clin. Med.*, 126:13–18 (1995).

(List continued on next page.)

*Primary Examiner*—William R. A. Jarvis
(74) *Attorney, Agent, or Firm*—Marshall, Gerstein, & Borun

(57) ABSTRACT

The present invention relates generally to pharmacological methods for the prevention of amelioration of sleep-related breathing disorders via administration of agents or combinations of agents that possess serotonin-related pharmacological activity.

37 Claims, 7 Drawing Sheets

OTHER PUBLICATIONS

Jacobs et al., "Reflex Apnea, Bradycardia, and Hypotension Produced by Serotonin and Phenyldiguanide Acting on the Nodose Ganglia of the Cat", *Circ. Res.*, 29:145–155 (1971).

Kraiczi et al., "Effect of Serotonin Uptake Inhibition on Breathing During Sleep and Daytime Symptoms on Obstructine Sleep Apnea", *Sleep*, 22:61–67 (1999).

Kubin et al., "Serotonergic Excitatory Drive To Hypoglossal Montoneurons in the Decerebrate Cat", *Neurosci. Lett.*, 139:243–248 (1992).

Mancia et al., In: Orem et al., eds., "Physiology in sleep," *Academic Press*, New York, NY, pp. 1–55 (1980).

McQueen et al., "Activation of P2X Receptors for Adenosine Triphosphate Evokes Cardiorespiratory Reflexes in Anesthetized Rats", *J. Physiol.*, 5073:843–855 (1998).

Mendelson et al., "Effects of Buspirone on Sleep and Respiration", *Am. Rev. Respir. Dis.*, 141:1527–1530 (1990).

Mendelson et al., "Buspirone Administration to Sleep Apnea Patients", *J. Clin. Psychopharmacol.*, 11:71–72 (1991).

Mendelson et al., "Periodic Cessation of Respiratory Effort During Sleep in Adult Rats", *Physiol. Behav.*, 43:229–234 (1988).

Morin, "Compared Effects of Serotonin on the Inspiratory Activity of Glossopharyngeal, Vagal, Hypoglossal and Cervical Motoneurons in Neonatal Rat Brain Stem–Spinal Cord Preparations", *Neurosci. Lett.*, 160:61–64 (1993).

Monti et al., "p–SPA, a Peripheral Adenosine $A_1$ Analogue, Reduces Sleep Apneas in Rats," *Pharmacol. Biochem. Behav.*, 53:341–345 (1996).

Monti, et al., "Adenosine Analogues Modulate the Incidence of Sleep Apneas in Rats," *Pharamcol. Biochem. Behav.*, 51(1):125–131 (1995).

Orem et al., "Breathing During Sleep and Wakefulness in the Cat", *Respir. Physiol.*, 30:265–289 (1977).

Phillipson, E., "Respiratory Adaptations in Sleep", *Annu. Rev. Physiol.*, 40:133–156 (1978).

Planès et al., "Effect of Celiprolol Treatment in Hypertensive Patients With Sleep Apnea", *Sleep*, 22:507–513 (1999).

Ponsonby et al., "Factors Related to Infant Apnoea and Cyanosis: A Population–Based Study", *J. Paediatr. Child Health*, 33:317–323 (1997).

Puzantian, "Mirtazapine, an Antidepressant", *Am. J. Heatlh–Syst. Pharm.*, 55:44–49 (1998).

Radulovacki et al., "Adenosine Analogs and Sleep in Rats," *J. Pharm. Exp. Ther.*, 228(2)268–274 (1984).

Radulovacki et al., "Serotonin 5–HT3–Receptor Antagonist GR 38032F Suppresses Sleep Apneas in Rats," *Sleep*, 21(2):131–136 (Mar., 1998).

Radulovacki et al., "Sleep Disordered Breathing: Hypotension Reduces Sleep Apneas in Zucker Lean and Zucker Obese Rats," *Sleep*, 19:767–773 (1996).

Rose et al., "Central Effects of 5–HT on Respiratory and Hypoglossal Activities in the Adult Cat", *Resp. . Physiol.*, 101:59–69 (1995).

Sampson et al., "Excitatory Effects of 5–Hydroxytryptamine, Veratridine, and Phenyl Diguanide on Sensory Ganglion Cells of the Nodose Ganglion of the Cat", *Life Sci.*, 15:2157–2165 (1975).

Sanders–Bush et al., 5–Hydroxytryptamine (Serotonin) Receptor Agonist and Antagonist, Chapter 11, pp. 249–263, 1996.

Sapru et al., "Effect of 5–Hydroxytryptamine on thr Peripheral Chemoreceptors in the Rat", *Res. Comm. Chem. Pathol. Pharmacol.*, 16:245–250 (1977).

Sato et al., "Sleep Apneas and Cardiac Arrhythmias in Freely Moving Rats", *Am. J. Physiol.*, 259:R282–R287 (1990).

Schmidt, "L–Tryptophan in the Treatment of Impaired Respiration in Sleep", *Bull. Eur. Physiol. Respir.*, 19:625–629 (1982).

Sieck et al., "Pneumotaxic Area Neuronal Discharge During Sleep–Waking States in the Cat", *Exp. Neurol.*, 67:79–102 (1980).

Sullivan, In: Orems et al., eds., "Physiology in sleep," *Academic Press*, New York, NY, pp. 213–272 (1980).

Szereda–Przestaszewska et al., "Effects of Vagal and Laryngeal Afferents on Apnoeic Response to Serotonin in Cats", *Respir. Physiol.*, 101:231–237 (1995).

Thomas et al., "Modification of Conditioned Apneas in Rats: Evidence for Cortical Involvement", *J. Appl. Physiol.*, 78:1215–1218 (1992).

Thomas et al., "A Model of Ventilatoy Instability Induced in the Unrestrained Rat", *J. Appl. Physiol.*, 73:1530–1536 (1995).

Veasey et al., "a Novel Serotonergic Compound Reduces Sleep–Disordered Breathing in the English BullDog", *Sleep Res.*, A529 (1997).

Veasey et al., "The Effects of Serotonin Antagonists in an Animal Model of Sleep–Disordered Breathing," *Am. J. Resp. Crit. Care Med.*, 153(2):776–786 (1996).

Wilken et al., "Treatment of Apneustic Respiratory Disturbance With a Serotonin–Receptor Agonist", *J. Pediatr.*, 130:89–94 (1997).

Yoshioka et al., "Effect of 5–Hydroxytryptamine on External Carotid Nerve Activity and its Blockade by GRE38032F in Anesthetized Rats", *Res. Comm. Chem. Pathol. Pharmacol.*, 74:39–45 (1991).

Yoshioka et al., "Pharmacological Characterization of 5–Hydroxytryptamine–Induced Apnea in the Rat," *J. Pharmacol. Exp. Ther.*, 260(2):917–924 (Jan., 1992).

Yoshioka et al., "Effect of a novel 5–Hydroxytryptamine 3–Antagonist, GRE38032F, on the 5–Hydroxytryptamine–Induced Increase in Carotid Sinus Nerve Activity in Rats", *J. Pharmacol. Exp. Ther.*, 250:637–641 (1989).

Zucker et al., "Reflex Cardiovascular and Respiratory Effects of Serotonin in Conscious and Anesthetized Dogs", *Circ. Res.* 47: 509–515 (1980).

Hudgel et al., *J. Appl. Physiol.*, 56:13–17 (1984).

Matsumoto, *Arch. Int Pharmacodyn. Ther.*, 254:282–292 (1981).

Sutton, *Pfllugers Arch.*, 389:181–187 (1981).

* cited by examiner

PHARMACOLOGICAL TREATMENT FOR SLEEP APNEA

This application is a 371 of PCT/US99/04347, filed Feb. 26, 1999, which claims priority to U.S. Provisional Application No. 60/076,216, filed Feb. 27, 1998, which is incorporated herein by reference in its entirety.

BACKGROUND OF THE INVENTION

1. Field of the Invention

This invention generally relates to methods for the pharmacological treatment of breathing disorders and, more specifically, to the administration of agents or compositions having serotonin-related receptor activity for the alleviation of sleep apnea (central and obstructive) and other sleep-related breathing disorders.

2. Related Technology

Over the past several years much effort has been devoted to the study of a discrete group of breathing disorders that occur primarily during sleep with consequences that may persist throughout the waking hours in the form of sleepiness, thereby manifesting itself into substantial economic loss (e.g., thousands of lost man-hours) or employment safety factors (e.g., employee non-attentiveness during operation of heavy-machinery). Sleep-related breathing disorders are characterized by repetitive reduction in breathing (hypopnea), periodic cessation of breathing (apnea), or a continuous or sustained reduction in ventilation.

In general sleep apnea is defined as an intermittent cessation of airflow at the nose and mouth during sleep. By convention, apneas of at least 10 seconds in duration have been considered important, but in most individuals the apneas are 20–30 seconds in duration and may be as long as 2–3 minutes. While there is some uncertainty as to the minimum number of apneas that should be considered clinically important, by the time most individuals come to attention of the medical community they have at least 10 to 15 events per hour of sleep.

Sleep apneas have been classified into three types: central, obstructive, and mixed. In central sleep apnea the neural drive to all respiratory muscles is transiently abolished. In obstructive sleep apneas, airflow ceases despite continuing respiratory drive because of occlusion of the oropharyngeal airway. Mixed apneas, which consist of a central apnea followed by an obstructive component, are a variant of obstructive sleep apnea. The most common type of apnea is obstructive sleep apnea.

Obstructive sleep apnea syndrome (OSAS) has been identified in as many as 24% of working adult men and 9% of similar women, with peak prevalence in the sixth decade. Habitual heavy snoring, which is an almost invariant feature of OSAS, has been described in up to 24% of middle aged men, and 14% of similarly aged women, with even greater prevalence in older subjects.

Obstructive sleep apnea syndrome's definitive event is the occlusion of the upper airway, frequently at the level of the oropharynx. The resultant apnea generally leads to a progressive-type asphyxia until the individual is briefly aroused from the sleeping state, thereby restoring airway patency and thus restoring airflow.

An important factor that leads to the collapse of the upper airway in OSAS is the generation of a critical subatmospheric pressure during the act of inspiration that exceeds the ability of the airway dilator and abductor muscles to maintain airway stability. Sleep plays a crucial role by reducing the activity of the muscles of the upper airways including the dilator and abductor muscles.

In most individuals with OSAS the patency of the airway is also compromised structurally and is therefore predisposed to occlusion. In a minority of individuals the structural compromise is usually due to obvious anatomic abnormalities, i.e, adenotonsillar hypertrophy, retrognathia, or macroglossia. However, in the majority of individuals predisposed to OSAS, the structural abnormality is simply a subtle reduction in airway size, i.e., "pharyngeal crowding." Obesity also frequently contributes to the reduction in size seen in the upper airways. The act of snoring, which is actually a high-frequency vibration of the palatal and pharyngeal soft tissues that results from the decrease in the size of the upper airway lumen, usually aggravates the narrowing via the production of edema in the soft tissues.

The recurrent episodes of nocturnal asphyxia and of arousal from sleep that characterize OSAS lead to a series of secondary physiologic events, which in turn give rise to the clinical complications of the syndrome. The most common manifestations are neuropsychiatric and behavioral disturbances that are thought to arise from the fragmentation of sleep and loss of slow-wave sleep induced by the recurrent arousal responses. Nocturnal cerebral hypoxia also may play an important role. The most pervasive manifestation is excessive daytime sleepiness. OSAS is now recognized as a leading cause of daytime sleepiness and has been implicated as an important risk factor for such problems as motor vehicle accidents. Other related symptoms include intellectual impairment, memory loss, personality disturbances, and impotence.

The other major manifestations are cardiorespiratory in nature and are thought to arise from the recurrent episodes of nocturnal asphyxia. Most individuals demonstrate a cyclical slowing of the heart during the apneas to 30 to 50 beats per minute, followed by tachycardia of 90 to 120 beats per minute during the ventilatory phase. A small number of individuals develop severe bradycardia with asystoles of 8 to 12 seconds in duration or dangerous tachyarrhythmias, including unsustained ventricular tachycardia. OSAS also aggravates left ventricular failure in patients with underlying heart disease. This complication is most likely due to the combined effects of increased left ventricular afterload during each obstructive event, secondary to increased negative intrathoracic pressure, recurrent nocturnal hypoxemia, and chronically elevated sympathoadrenal activity.

Central sleep apnea is less prevalent as a syndrome than OSAS, but can be identified in a wide spectrum of patients with medical, neurological, and/or neuromuscular disorders associated with diurnal alveolar hypoventilation or periodic breathing. The definitive event in central sleep apnea is transient abolition of central drive to the ventilatory muscles. The resulting apnea leads to a primary sequence of events similar to those of OSAS. Several underlying mechanisms can result in cessation of respiratory drive during sleep. First are defects in the metabolic respiratory control system and respiratory neuromuscular apparatus. Other central sleep apnea disorders arise from transient instabilities in an otherwise intact respiratory control system.

Many healthy individuals demonstrate a small number of central apneas during sleep, particularly at sleep onset and in REM sleep. These apneas are not associated with any physiological or clinical disturbance. In individuals with clinically significant central sleep apnea, the primary sequence of events that characterize the disorder leads to prominent physiological and clinical consequences. In those individuals with central sleep apnea alveolar hypoventilation syndrome, daytime hypercapnia and hypoxemia are usually evident and the clinical picture is dominated by a history of recurrent respiratory failure, polycythemia, pulmonary hypertension, and right-sided heart failure. Complaints of sleeping poorly, morning headache, and daytime fatigue and sleepiness are also prominent. In contrast, in individuals whose central sleep apnea results from an instability in respiratory drive, the clinical picture is dominated by features related to sleep disturbance, including recurrent nocturnal awakenings, morning fatigue, and daytime sleepiness.

Currently, the most common and most effective treatment, for adults with sleep apnea and other sleep-related breathing disorders are mechanical forms of therapy that deliver positive airway pressure (PAP). Under PAP treatment, an individual wears a tight-fitting plastic mask over the nose when sleeping. The mask is attached to a compressor, which forces air into the nose creating a positive pressure within the patient's airways. The principle of the method is that pressurizing the airways provides a mechanical "splinting" action, which prevents airway collapse and therefore, obstructive sleep apnea. Although an effective therapeutic response is observed in most patients who undergo PAP treatment, many patients cannot tolerate the apparatus or pressure and refuse treatment. Moreover, recent covert monitoring studies clearly demonstrate that long-term compliance with PAP treatment is very poor.

A variety of upper airway and craniofacial surgical procedures have been attempted for treatment of OSAS. Adenotonsillectomy appears to be an effective cure for OSAS in many children, but upper airway surgery is rarely curative in adult patients with OSAS. Surgical "success" is generally taken to be a 50% reduction in apnea incidence and there are no useful screening methods to identify the individuals that would benefit from the surgery versus those who would not derive a benefit.

Pharmacological treatments of several types have been attempted in patients with sleep apnea but, thus far, none have proven to be generally useful. A recent systematic review of these attempts is provided by Hudgel [*J. Lab. Clin. Med.*, 126:13–18 (1995)]. A number of compounds have been tested because of their expected respiratory stimulant properties. These include (1) acetazolamide, a carbonic anhydrase inhibitor that produced variable improvement in individuals with primary central apneas but caused an increase in obstructive apneas, (2) medroxyprogesterone, a progestin that has demonstrated no consistent benefit in OSAS, and (3) theophylline, a compound usually used for the treatment of asthma, which may benefit patients with central apnea but appears to be of no use in adult patients with obstructive apnea.

Other attempted pharmacological treatment includes the administration of adenosine, adenosine analogs and adenosine reuptake inhibitors (U.S. Pat. No. 5,075,290). Specifically, adenosine, which is a ubiquitous compound within the body and which levels are elevated in individuals with OSAS, has been shown to stimulate respiration and is somewhat effective in reducing apnea in an animal model of sleep apnea.

Other possible pharmacological treatment options for OSAS include agents that stimulate the brain activity or are opioid antagonists. Specifically, since increased cerebral spinal fluid opioid activity has been identified in OSAS, it is a logical conclusion that central stimulants or opioid antagonists would be a helpful treatment of OSAS. In reality, doxapram, which stimulates the central nervous system and carotid body chemoreceptors, was found to decrease the length of apneas but did not alter the average arterial oxygen saturation in individuals with obstructive sleep apnea. The opioid antagonist naloxone, which is known to stimulate ventilation was only slightly helpful in individuals with obstructive sleep apnea.

Because OSAS is strongly correlated with the occurrence of hypertension, agents such as angiotensin-converting enzyme (ACE) inhibitors may be of benefit in treating OSAS individuals with hypertension but this does not appear to be a viable treatment for OSAS itself.

Finally, several agents that act on neurotransmitters and neurotransmitter systems involved in respiration have been tested in individuals with OSAS. Most of these compounds have been developed as anti-depressant medications that work by increasing the activity of monoamine neurotransmitters including norepinephrine, dopamine, and serotonin. Protriptyline, a tricyclic anti-depressant, has been tested in several small trials with variable results and frequent and significant side effects. As serotonin may promote sleep and stimulate respiration, tryptophan, a serotonin precursor and selective serotonin reuptake inhibitors have been tested in individuals with OSAS. While a patent has been issued for the use of the serotonin reuptake inhibitor, fluoxetine (U.S. Pat. No. 5,356,934), initial evidence suggests that these compounds may yield measurable benefits in only approximately 50% of individuals with OSAS. Therefore in view of the fact that the only viable treatment for individuals suffering from sleep-related breathing disorders is a mechanical form of therapy (PAP) for which patient compliance is low, and that hopes for pharmacological treatments have yet to come to fruition, there remains a need for simple pharmacologically-based treatments that would offer benefits to a broad base of individuals suffering from a range of sleep-related breathing disorders. There also remains a need for a viable treatment of sleep-related breathing disorders that would lend itself to a high rate of patient compliance.

SUMMARY OF THE INVENTION

The invention is directed to providing pharmacological treatments for the prevention or amelioration of sleep-related breathing disorders.

The present invention is directed to methods for the prevention or amelioration of sleep-related breathing disorders, the method comprising the administration of an effective dose of serotonin receptor antagonist to a patient in need of such therapy. The present invention is also directed to methods comprising the administration of a combination of serotonin receptor antagonists for the prevention or amelioration of sleep-related breathing disorders. The combination of serotonin receptor antagonists may be directed to a single serotonin receptor subtype or to more than one serotonin receptor subtype.

The present invention is further directed to methods comprising the administration of a combination of serotonin receptor antagonists in conjunction with a combination of serotonin receptor agonists for the prevention or amelioration of sleep-related breathing disorders. The combination of serotonin receptor antagonists as well as the combination of receptor agonist may be directed to a single serotonin receptor subtype or to more than one serotonin receptor subtype.

The present invention is also directed to methods comprising the administration of a combination of serotonin receptor antagonists in conjunction with a $\alpha_2$ adrenergic receptor subtype antagonist for the prevention or amelioration of sleep-related breathing disorders. The combination of serotonin receptor antagonists may be directed to a single serotonin receptor subtype or to more than one serotonin receptor subtype.

Routes of administration for the foregoing methods may be by any systemic means including oral, intraperitoneal, subcutaneous, intravenous, intramuscular, transdermal, or by other routes of administration. Osmotic mini-pumps and timed-released pellets or other depot forms of administration may also be used. The only limitation being that the route of administration results in the ultimate delivery of the pharmacological agent to the appropriate receptor.

Sleep-related breathing disorders include, but are not limited to, obstructive sleep apnea syndrome, apnea of prematurity, congenital central hypoventilation syndrome, obesity hypoventilation syndrome, central sleep apnea syndrome, Cheyne-Stokes respiration, and snoring.

Exemplary serotonin receptor antagonists include, but are not limited to ondansetron (GR38032F), ketanserin, risperidone, cyproheptadine, clozapine, methysergide, granisetron, mianserin, ritanserin, cinanserin, LY-53,857, metergoline, LY-278,584, methiothepin, p-NPPL, NAN-190, piperazine, SB-206553, SDZ-205,557, 3-tropanyl-indole-3-carboxylate, 3-tropanyl-indole-3-carboxylate methiodide, and other serotonin receptor antagonists.

Exemplary serotonin receptor agonists include, but are not limited to 8-OH-DPAT, sumatriptan, L694247 (2-[5-[3-(4-methylsulphonylamino)benzyl-1,2,4-oxadiazol-5-yl]-1H-indol-3yl]ethanamine), buspirone, alnitidan, zalospirone, ipsapirone, gepirone, zolmitriptan, risatriptan, 311C90, $\alpha$-Me-5-HT, BW723C86 (1-[5(2-thienylmethoxy)-1H-3-indolyl[propan-2-amine hydrochloride), and MCPP (m-chlorophenylpiperazine).

Exemplary $\alpha_2$ adrenergic receptor antagonist include, but are not limited to phenoxybenzamine, phentolamine, tolazoline, terazosine, doxazosin, trim azosin, yohimbine, indoramin, ARC239, and prazosin.

DETAILED DESCRIPTION OF THE INVENTION

Figure 1:
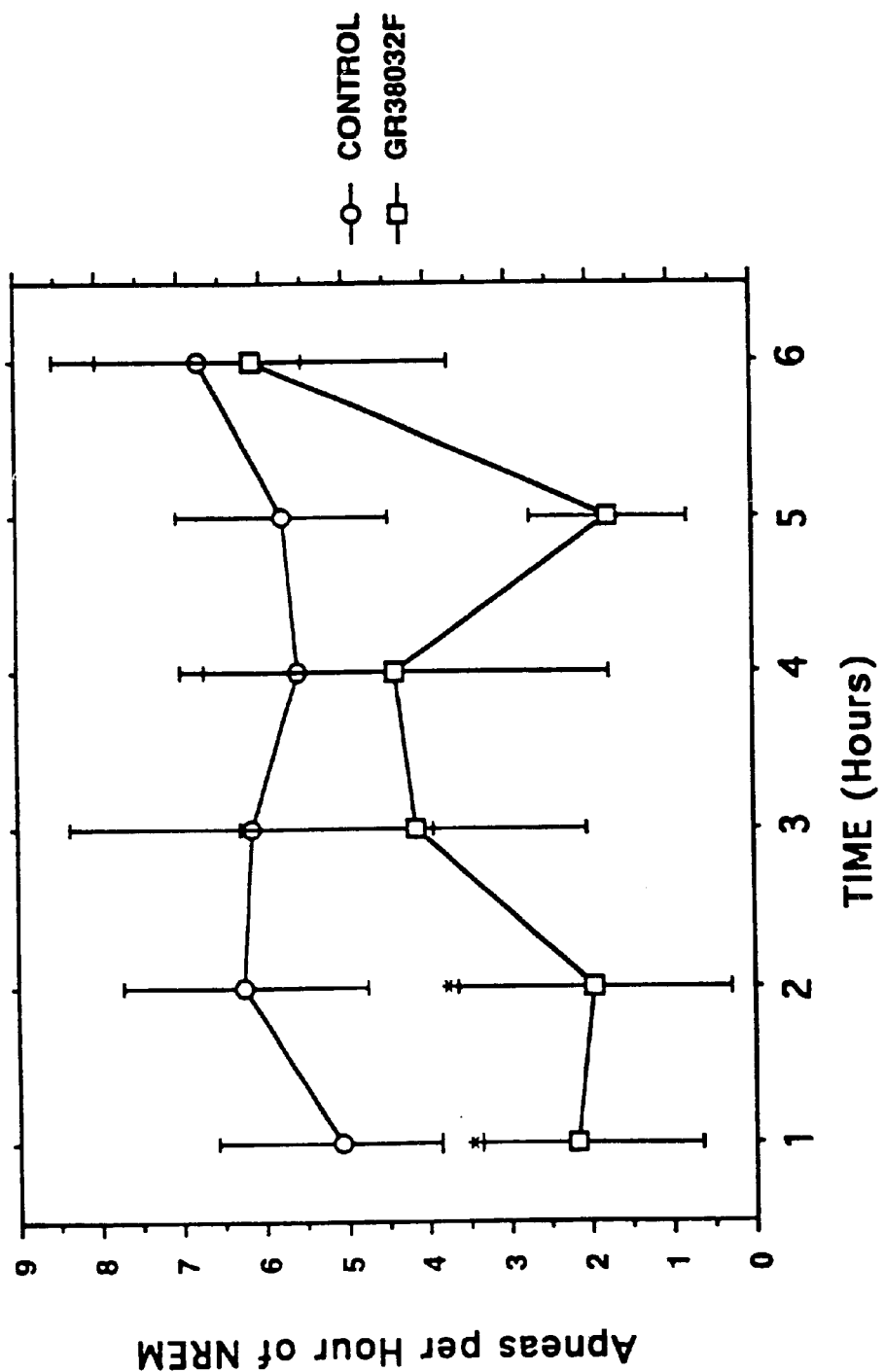
FIG. 1 illustrates the effect of serotonin antagonist GR38032F (ondansetron) on the rate of apneas per hour of non-rapid eye movement (NREM) sleep as compared to control. Each data point on the figure represents the mean ± the standard error for 9 rats (p=0.007 versus control).

Previous studies on the effect of serotonin or serotonin analogs on respiration in several anesthetized (see below) animal species have demonstrated variable responses. For example, administration of serotonin has been shown to cause an increase in the respiratory rate with a decrease in tidal volume in rabbits, but an increase in the tidal volume in dogs [Matsumoto, Arch. Int Pharnacodyn. Ther., 254:282–292 (1981); Armstrong et al., J. Physiol. (Lond.), 365:104 P (1985); Bisgard et al., Resp. Physiol. 37:61–80 (1979); Zucker et al. Circ. Res. 47: 509–515 (1980). In studies with cats, serotonin administration produced hyperventilation occasionally preceded by apnea [Black et al., Am. J. Physiol., 223:1097–1102 (1972); Jacobs et al., Circ. Res., 29:145–155 (1971)], or immediate apnea followed by rapid shallow breathing [Szereda-Przestaszewska et al., Respir. Physiol., 101:231–237 (1995)].

Administration of 2-methyl-5-hydroxytryptamine, a selective 5-hydroxytryptamine$_3$ receptor agonist, in cat studies caused apnea [Butler et al. Br. J. Pharmacol., 94:397–412 (1988)]. Intravenous administration of serotonin, 2-methyl-5-hydroxytryptamine or a high dose of $\alpha$-methyl-5-hydroxytryptamine, a 5-hydroxytryptamine$_2$ receptor agonist, produced transient apnea, the duration of which increased in a dose-dependent fashion. This response was significantly antagonized by GR38032F (1,2,3,9-tetrahydro-9-methyl-3-[(2-methylirnidazol-1-yl)methyl] carbazole-4-one, hydrochloride, dihydrate), a selective 5-hydroxytryptamine$_3$ receptor antagonist [Butler et al. Br. J. Pharmacol., 94:397–412 (1988); Hagan et al., Eur. J. Pharmacol., 138:303–305 (1987)] as well as by ketanserine and methysergide, 5-hydroxytryptamine$_2$ receptor antagonists [Yoshioka et al., J. Pharmacol. Exp. Ther., 260:917–924 (1992)]. In newborn rats, administration of serotonin precursor L-tryptophan, which activated central serotonin biosynthesis, produced recurrent episodes of obstructive apnea often followed by central apneas [Hilaire et al., J. Physiol., 466:367–382 (1993); Morin, Neurosci. Lett., 160:61–64 (1993)].

While the foregoing studies revealed significant information concerning the involvement of serotonin in the development of apneas, as stated above one significant problem with all of these studies is that the animals were anesthetized, and thus any results obtained could not be attributed to a specific serotonin agonist or antagonist, i.e., an interaction with the anesthesia or abnormal physiologic conditions associated with the anesthetic could not be ruled out.

Activity at serotonin receptors may also promote spontaneous sleep-related central apneas, which have been reported in rats, [Mendelson et al., *Physiol. Behav.*, 43:229–234 (1988); Sato et al. *Am. J. Physiol.*, 259: R282-R287 (1990); Monti et al., *Pharmacol. Biochem. Behav.*, 125–131 (1995); Monti et al., *Pharmacol. Biochem. Behav.*, 53:341–345 (1996); Thomas et al., . *J. Appl. Physiol.*, 78:215–218 (1992); Thomas et al., *J. Appl. Physiol.*, 73:1530–1536 (1995); Carley et al. *Sleep*, 19:363–366 (1996); Carley et al., *Physiol. Behav.*, 59:827–831 (1996); Radulovacki et al., *Sleep*, 19:767–773 (1996); Christon et al., *J. Appl. Physiol.*, 80:2102–2107 (1996)]. In order to test this hypothesis, experiments were conducted to test the effects of a serotonin antagonist in freely moving animals in order to assess whether blockade of serotonin receptors would inhibit expression of spontaneous apneas during NREM sleep and REM sleep. Experiments were also conducted to test the effects of serotonin and serotonin antagonists, singly and in combination, in freely moving animals in order to assess whether increased serotonergic activity at peripheral serotonin receptors may promote sleep apneas.

The following examples illustrate the effects of administration of serotonin receptor antagonists, and in particular GR38032F, to cause suppression of central apneas during non rapid eye movement (NREM) and especially during rapid eye movement (REM) sleep. This effect was associated with increased respiratory drive but did not cause cardiovascular changes at the dose tested.

The following examples also illustrate the effects of serotonin administration to induce spontaneous apnea expression, which was completely antagonized via the administration of serotonin receptor antagonists, and in particular GR38032F.

The following examples further describe the pharmacological profiles best suited for single agents or combinations of agents to successfully prevent or ameliorate sleep-related breathing disorders, i.e., (a) a single agent or combination of agents having either 5-hydroxytryptamine$_2$ or 5-hydroxytryptamine$_3$ receptor subtype antagonistic activity or both;

(b) a single agent or combination of agents having either 5-hydroxytryptamine$_2$ or 5-hydroxytryptamine$_3$ receptor subtype antagonistic activity or both in conjunction with either 5-hydroxytryptamine$_1$ or 5-hydroxytryptamine$_2$ receptor subtype agonistic activity or both; or (c) a single agent or combination of agents having either 5-hydroxytryptamine$_2$ or 5-hydroxytryptamine$_3$ receptor subtype antagonistic activity or both in conjunction with $\alpha_2$ adrenergic receptor subtype antagonistic activity.

Further aspects of the invention and embodiments will be apparent to those skilled in the art. In order that the present invention is fully understood, the following examples are provided by way of exemplification only and not by way of limitation.

Example 1 describes the preparation of the animals for treatment with either serotonin antagonists or agonists or both and subsequent physiological recording and testing.

Example 2 describes the methods for the physiological recording of treatment and control animals and results obtained from administration of a serotonin antagonist.

Example 3 describes results obtained from the administration of serotonin followed by the administration of a serotonin receptor antagonist.

Example 4 describes agents or compositions that posses a specific serotonin-related pharmacological activity that is used to effectively suppress or prevent sleep-related breathing disorders.

The following examples are illustrative of aspects of the present invention but are not to be construed as limiting.

EXAMPLE 1

Preparation of Animals for Physiological Testing and Recording

Adult, male Sprague-Dawley rats (Sasco-King, Wilmington, Mass.; usually 8 per test group; 300 g) were maintained on a 12-hour light (08:00–20:00 hour)/12-hour dark (20:00–08:00 hour) cycle for one week, housed in individual cages and given ad libitum access to food and water. Following the one week of acclimatization, animals were subjected to the following surgical procedures.

Acclimatized animals were anesthetized for the implantation of cortical electrodes for electroencephalogram (EEG) recording and neck muscle electrodes for electromyogram (EMG) recording using a mixture of ketamine (Vedco, Inc., St. Joseph, Mo.; 100 mg/ml) and acetylpromazine (Vedco, Inc., St. Joseph, Mo.; 10 mg/ml; 4:1, volume/volume) at a volume of 1 ml/kg body weight. The surface of the skull was exposed surgically and cleaned with a 20% solution of hydrogen peroxide followed by a solution of 95% isopropyl alcohol. Next, a dental preparation of sodium fluoride (Flura-GEL®, Saslow Dental, Mt. Prospect, Ill.) was applied to harden the skull above the parietal cortex and allowed to remain in place for 5 minutes. The fluoride mixture was then removed from the skull above the parietal cortex. The EEG electrodes consisting of four stainless steel machine screws, having leads attached thereto, were threaded into the skull to rest on the dura over the parietal cortex. A thin layer of Justi® resin cement (Saslow Denial, Mt. Prospect, Ill.) was applied to cover the screw heads (of screws implanted in the skull) and surrounding skull to further promote the adhesion of the implant. EMG electrodes consisting of two ball-shaped wires were inserted into the bilateral neck musculature. All leads (i.e., EEG and EMG leads) were soldered to a miniature connector (39F1401, Newark Electronics, Schaumburg, Ill.). Lastly, the entire assembly was fixed to the skull with dental cement.

After surgery, all animals were allowed to recover for one week before being subjected to another surgery that involved implantation of a radiotelemetry transmitter (TA11-PXT, Data Sciences International, St. Paul, Minn.) for monitoring blood pressure (BP) and heart period (HP), estimated as pulse interval. After the animals were anesthetized (as described above), the hair from the subxiphoid space to the pelvis was removed. The entire area was scrubbed with iodine and rinsed with alcohol and saline. A 4–6 cm midline abdominal incision was made to allow good visualization of the area from the bifurcation of the aorta to the renal arteries. A retractor was used to expose the contents of the abdomen and the intestine was held back using saline moistened gauze sponges. The aorta was dissected from the surrounding fat and connective tissues using sterile cotton applicators. A 3-0 silk suture was placed beneath the aorta and traction was applied to the suture to restrict the blood flow. Then the implant (TA11-PXT) was held by forceps while the aorta was punctured just cranial to the bifurcation using a 21-gauge needle bent at the beveled end. The tip of the catheter was inserted under the needle using the needle as a guide until the thin-walled BP sensor section was within the vessel. Finally, one drop of tissue adhesive (Vetbond®, 3M, Minneapolis, Minn.) was applied to the puncture site and covered with a small square of cellulose fiber (approximately 5 mm$^2$) so as to seal the puncture after catheter insertion. The radio implant was attached to the abdominal wall by 3-0 silk suture, and the incision was closed in layers. After the second surgery, animals were again allowed a one week recovery period prior to administration of the serotonin receptor antagonist and subsequent physiological recording.

EXAMPLE 2

Physiological Recording and Suppression of Apneas

Physiological parameters (see below) from each animal were recorded on 2 occasions in random order, with recordings for an individual animal separated for at least 3 days. Fifteen minutes prior to each recording each animal received a systemic injection (1 ml/kg intraperitoneal bolus injection) of either saline (control) or 1 mg/kg of ondansetron (GR38032F; 1,2,3,9-tetrahydro-9-methyl-3-[(2-methylimidazol-1-yl)methyl]carbazole-4-one, hydrochloride, dihydrate; Glaxo Wellcome, Inc., Research Triangle Park, N.C.). Polygraphic recordings were made from hours 10:00–16:00.

Respiration was recorded by placing each animal, unrestrained, inside a single chamber plethysmograph (PLYUN1R/U; Buxco Electronics, Sharon, Conn.; dimension 6 in.×10 in.×6 in.) ventilated with a bias flow of fresh room air at a rate of 2 L/min. A cable plugged onto the animal's connector and passed through a sealed port was used to carry the bioelectrical activity from the head implant. Respiration, blood pressure, EEG activity, and EMG activity were displayed on a video monitor and simultaneously digitized 100 times per second and stored on computer disk (Experimenter's Workbench; Datawave Technologies, Longmont, Colo.).

Sleep and waking states were assessed using the biparietal EEG and nuchal EMG signals on 10-second epochs as described by Bennington et al. [Sleep, 17:28–36 (1994)]. This software discriminated wakefulness (W) as a high frequency low amplitude EEG with a concomitant high EMG tone, NREM sleep by increased spindle and theta activity together with decreased EMG tone, and REM sleep by a low ratio of a delta to theta activity and an absence of EMG tone. Sleep efficiency was measured as the percentage of total recorded epochs staged as NREM or REM sleep.

An accepted physiological animal model [rat; Monti, et al., Pharamcol. Biochem. Behav., 51:125–131 (1995)] of spontaneous sleep apnea was used to assess the effects of GR38032F. More specifically, sleep apneas, defined as cessation of respiratory effort for at least 2.5 seconds, were scored for each recording session and were associated with the stage of sleep in which they occurred: NREM or REM sleep. The duration requirement of 2.5 seconds represented at least 2 "missed" breaths, which is therefore analogous to a 10 second apnea duration requirement in humans, which also reflects 2–3 missed breaths. The events detected represent central apneas because decreased ventilation associated with obstructed or occluded airways would generate an increased plethysmographic signal, rather than a pause. An apnea index (AI), defined as apneas per hour in a stage were separately determined for NREM and REM sleep. The effects of sleep stage (NREM vs. REM) and injection (control vs. GR30832F) were tested using ANOVA with repeated measures. Multiple comparisons were controlled using Fisher's protected least significant difference (PLSD). In addition, the timing and volume of each breath were scored by automatic analysis (Experimenters' Workbench; Datawave Technologies, Longmont, Colo.). For each animal the mean respiratory rate (RR) and minute ventilation (MV) was computed for W throughout the 6 hour control recording and used as a baseline to normalize respiration during sleep and during GR38032F administration in that animal. One way ANOVA was also performed by non-parametric (Kruskal-Wallis) analysis. Conclusions using parametric and non-parametric ANOVA were identical in all cases.

Similar software (Experimenters' Workbench; Datawave Technologies, Longmont, Colo.) was employed to analyze the blood pressure waveform; for each beat of each recording, systolic (SBP) and diastolic (DBP) blood pressures and pulse interval were measured. The pulse interval provided a beat by beat estimate of HP. Mean BP (MBP) was estimated according to the weighted average of SBP and DBP for each beat: MBP=DBP+(SBP-DBP)/3. The parameters for each beat were also classified according to the sleep/wake state and recording hour during which they occurred.

Figure 2:
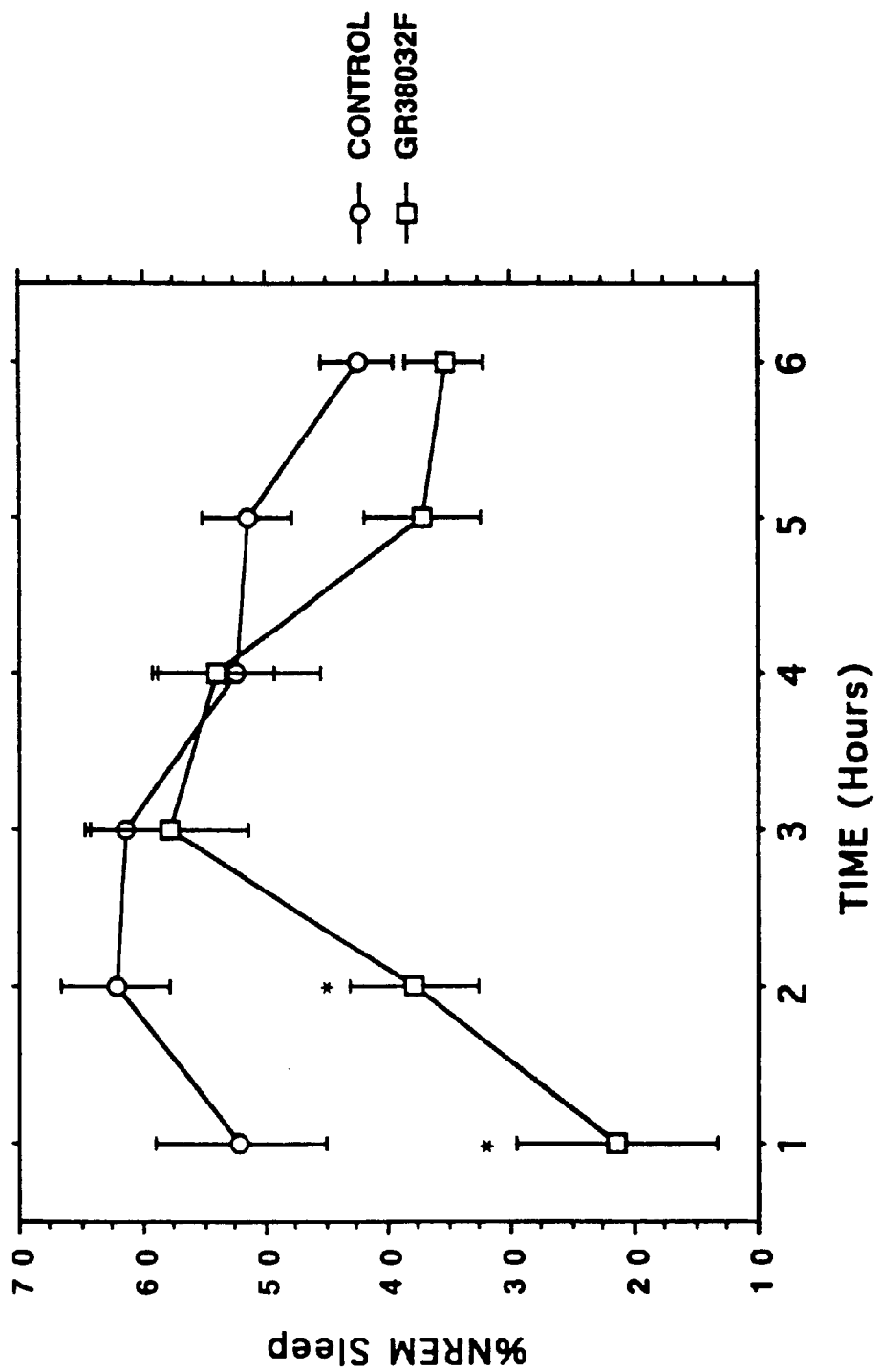
FIG. 2 shows the effect of the serotonin antagonist GR38032F (ondansetron) on the percentage of total recording time spent in NREM sleep as compared to control. Each data point represents the mean ± the standard error for 9 rats (p=0.0001 versus control).

Results of the administration of the serotonin antagonist GR38032F on the rate of apneas per hour of NREM sleep during the 6 hours of polygraphic recording (see FIG. 1) demonstrated no significant effect of treatment or time over 6 hours (two-way ANOVA). However, there was a significant suppression of apneas during the first 2 hours of recording as determined by paired t-tests (p<0.01 for each). This respiratory effect was associated with a significant suppression of NREM sleep by the GR38032F during the first 2 hours as demonstrated in FIG. 2. The percentage of NREM sleep in 6 hour recordings was lower in GR38032F administered rats than in controls, but the decrease reached statistical significance only during the first 2 hours of the recordings (p<0.001).

Figure 3:
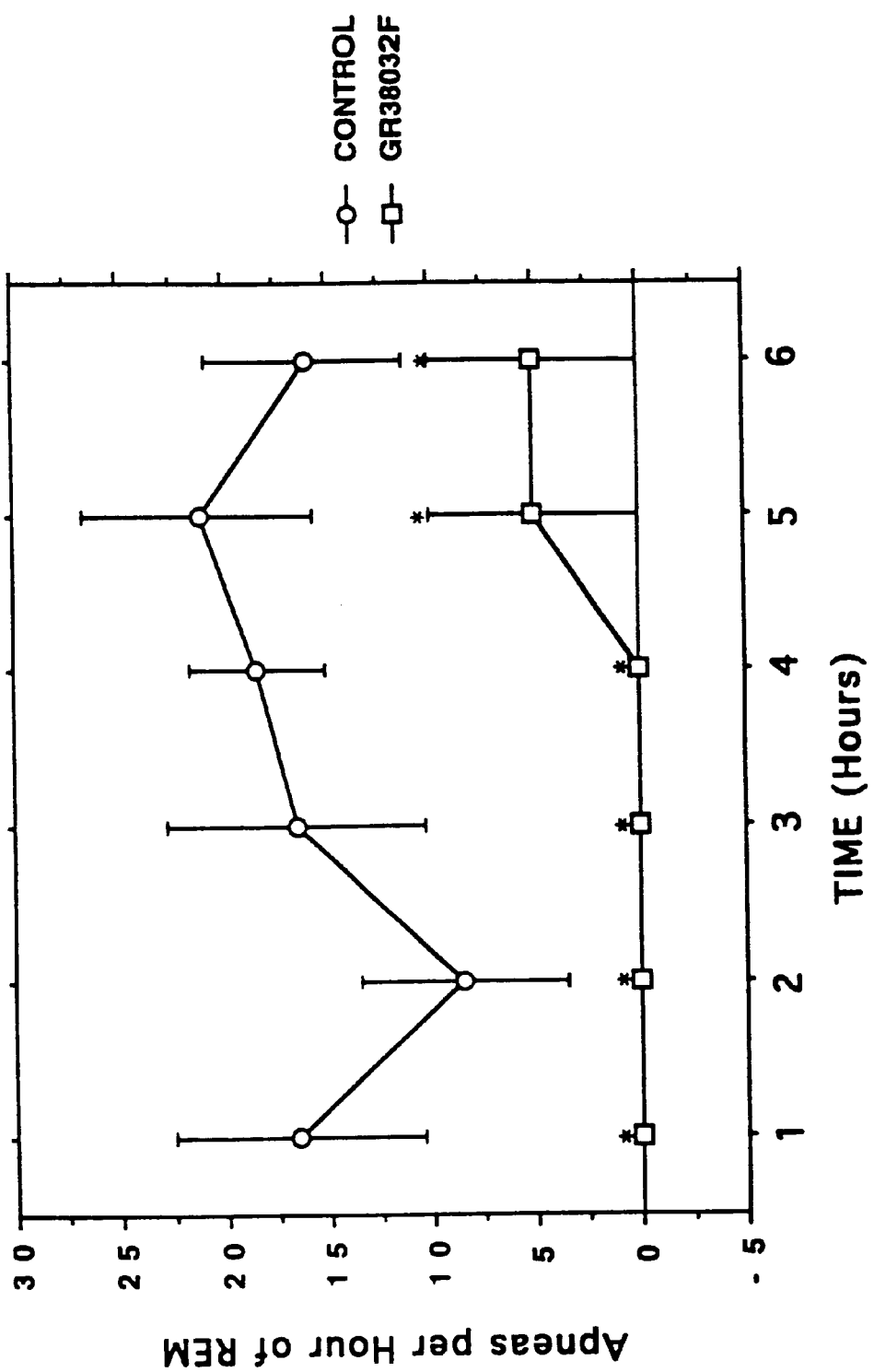
FIG. 3 shows the effect of the serotonin antagonist GR38032F (ondansetron) on the rate of apneas per hour of rapid-eye-movement (REM) sleep as compared to control. Each data point represents the mean ± the standard error for 9 rats (p=0.01 versus control).

Results further indicated a significant suppressant effect of GR38032F on REM sleep apneas throughout the 6 hour recording period (p=0.01 for drug effect on 2-way ANOVA; see FIG. 3). This effect was particularly manifest during the first 4 hours of recordings, during which no animal exhibited a single spontaneous apnea in REM sleep. This effect was not a simple reflection of REM suppression during the first 4 hours.

Figure 4:
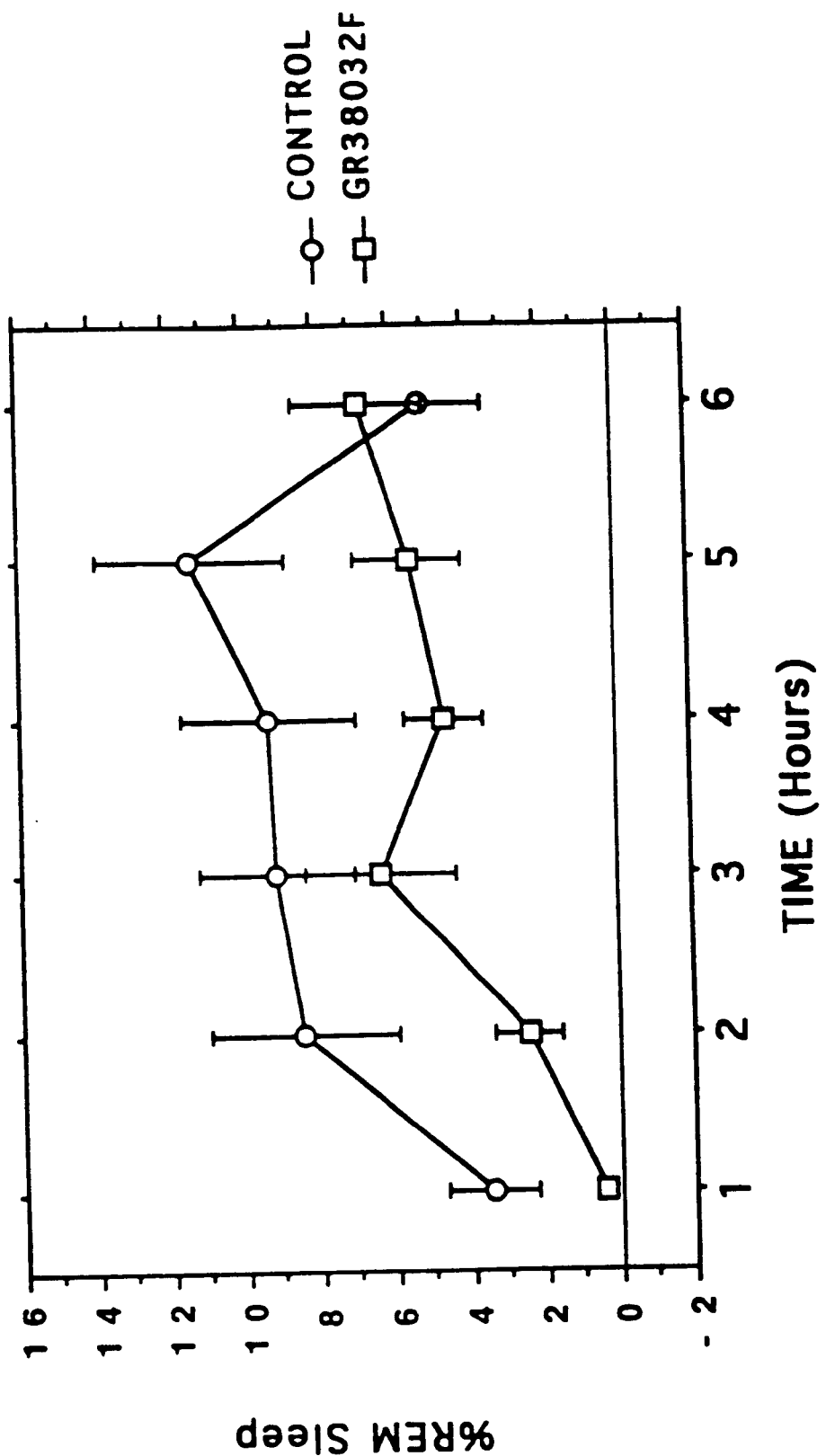
FIG. 4 illustrates the effect of the serotonin antagonist GR38032F (ondansetron) on the percentage of total recording time spent in REM sleep as compared to control. Each data point represents the mean ± the standard error for 9 rats.

Results set forth in FIG. 4 show that GR38032F did not significantly affect REM sleep. Although REM sleep in drug treated animals was lower than in corresponding controls it did not reach statistical significance overall or during any single recording hour.

Figure 5:
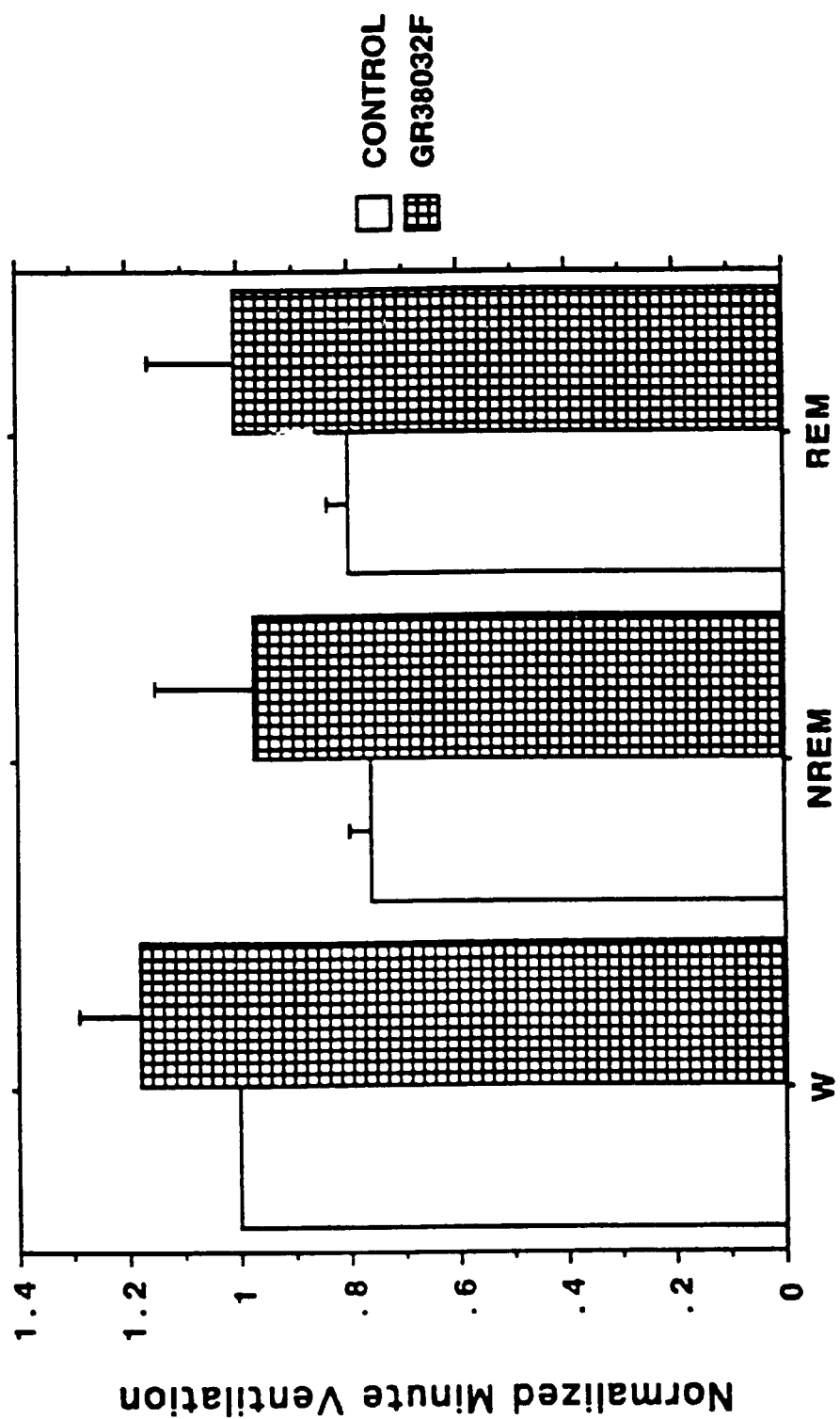
FIG. 5 shows the effects of the serotonin antagonist GR38032F (ondansetron) on the rate of normalized minute ventilation during wakefulness, NREM and REM sleep as compared to control. Each data bar represents the mean ± the standard error over 6 recording hours with all animals (n=9) pooled (minute ventilation was significantly larger following GR38032F administration in all behavioral states; p<0.03 versus control).

Results of the administration of GR38032F on the normalized minute ventilation during W (wake), NREM (non-rapid eye movement) sleep, and REM (rapid eye movement) sleep (see FIG. 5) indicate a significant stimulation of ventilation during all behavioral states (p=0.03 for each). Finally, results indicate that GR38032F had no effect on any cardiovascular variable (MBP and HP during W, NREM, and REM sleep) measured (p>0.1 for each variable; see Table 1).

TABLE 1

Effects of GR38032F on Cardiovascular Variables

| | Mean BP (mm Hg) | | | HP (msec) | | |
|---|---|---|---|---|---|---|
| | W | NREM | REM | W | NREM | REM |
| Control | 111 ± 18 | 110 ± 18 | 108 ± 18 | 174 ± 5 | 181 ± 5 | 185 ± 6 |
| GR38032F | 113 ± 18 | 112 ± 17 | 110 ± 17 | 183 ± 3 | 189 ± 3 | 190 ± 3 |

All values are mean ± SE.

Overall these results indicate that the manipulation of serotonergic systems can exert a potent influence on the generation of central apneas in both REM and NREM sleep. Specifically the present findings indicate that systemic administration of a 5-hydroxytryptamine$_3$ receptor antagonist suppresses spontaneous apnea expression; completely abolishing REM-related apnea for at least 4 hours after intraperitoneal injection. This apnea suppression was associated with a generalized respiratory stimulation that was observed as increased minute ventilation during both waking and sleep. These significant respiratory effects were observed at a dose which caused no change in heart rate or blood pressure, even during the first 2 hours, when respiration was maximal.

Those of skill in the art will recognize that exemplary serotonin receptor antagonists include, but are not limited to (a) ketanserin, cinanserin, LY-53,857, metergoline, LY-278, 584, methiothepin, p-NPPL, NAN-190, piperazine, SB-206553, SDZ-205,557, 3-tropanyl-indole-3-carboxylate, 3-tropanyl-indole-3-carboxylate methiodide, and methysergide (Research Biochemicals, Inc., Natick, Mass.); (b) risperidone (Janssen Pharmaceutica, Titusville, N.J.); (c) cyproheptadine, clozapine, mianserin, and ritanserin (Sigma Chemical Co., St. Louis, Mo.); (d) granisetron (SmithKline Beecham, King of Prussia, Pa.); and other serotonin receptor antagonists may be used to prevent or ameliorate sleep-related breathing disorders. Further, those of skill in the art will also recognize that the results discussed above may be easily correlated to other mammals, especially primates (e.g., humans).

EXAMPLE 3

Induction and Suppression of Sleep Apneas

Administration of serotonin or serotonin analogs produced variable respiratory responses in anesthetized animals of several species (see above, DETAILED DESCRIPTION OF THE INVENTION). As shown above in Example 2, intraperitoneal administration of 1 mg/kg GR38032F, a selective 5-hydroxytryptamine$_3$ receptor antagonist, suppressed spontaneous central apneas. This effect was especially prominent in REM sleep, during which apneas were completely abolished for at least 4 hours following injection. The apnea suppressant effect of GR38032F was paralleled by increased respiratory drive, but BP and heart rate changes were absent at the dose tested.

Suppression of spontaneous apneas during natural sleep by GR38032F (see Example 2) is consistent with prior studies in anesthetized rats, wherein 5-hydroxytryptamine and 2-methyl-5-hydroxytryptamine, a selective 5-HT$_3$ receptor agonist, provoked central apneas that were antagonized by GR38032F. Since 5-hydroxytryptamine does not penetrate the blood-brain barrier (BBB), these results (from the prior studies) indicate that stimulation of peripheral 5-hydroxytryptamine receptors, and more particularly 5-hydroxytryptamine$_3$ receptors seemed to have provoked the occurrence of central apneas. In view of that study, performed in anesthetized animals, as well as our study (described in Example 2 above) in freely moving rats with respect to administration of GR38032F, we studied the ability of increased serotonergic activity at peripheral 5-hydroxytryptamine receptors, and more specifically, 5-hydroxytryptamine$_3$ receptors to promote spontaneous sleep-related central apneas and whether any induction of apneas would be susceptible to antagonism by administration of 5-hydroxytryptamine receptor antagonists.

Ten adult male Sprague-Dawley rats (Sasco-King, Wilmington, Mass.; 300 g) were maintained on a 12-h light (08:00–20:00 hour)/12-hour dark (20:00–08:00) cycle for one week, housed in individual cages, and given ad libitum access to food and water. Following the one week of acclimatization, animals were prepared for physiological testing via the surgical procedures (i.e., implantation of cortical electrodes for EEG recording and neck muscle electrodes for EMG recording, implantation of a radiotelemetry transmitter for BP and HP monitoring) as set forth above in Example 1. After completion of the surgical procedures, animals were allowed a one week recovery period prior to use in the present study.

Each animal was recorded on four occasions, with recordings for an individual animal separated by at least three days. Fifteen minutes prior to each recording, each animal received (via intraperitoneal injection), in random order, one of the following: (a) saline solution (control); (b) 0.79 mg/kg serotonin; (c) 0.1 mg/kg GR38032F plus 0.79 mg/kg serotonin; or (d) 0.1 mg/kg GR38032F. For the GR38032F+serotonin test group, 0.1 mg/kg GR38032F was administered at time 09:30 followed by 0.79 mg/kg serotonin at time 09:45. Polygraphic recordings were made from 10:00–16:00.

Respiration BP, EEG, and EMG data were determined and recorded via the experimental procedure as specifically set forth above in Example 2. As in Example 2, sleep apneas, defined as cessation of respiratory effort for at least 2.5 s, were scored for each recording session and were associated with the stage in which they occurred: NREM or REM sleep. The duration requirement of 2.5 s represents at least two "missed" breaths, which is analogous to a 10-s apnea duration requirement in humans.

The effects of sleep stage (NREM vs REM) and injection (control vs. administration of either serotonin alone, GR38032F+serotonin, or GR38032F alone) on apnea indexes, respiratory pattern, BP, and HP were tested using analysis of variance (ANOVA) with repeated measures. Multiple comparisons were controlled using Fisher's protected least-significance difference (PLSD). One-way ANOVA was also performed by nonparametric (Kruskal-Wallis) analysis. Conclusions using parametric and nonparametric ANOVA were identical in all cases.

Figure 6:
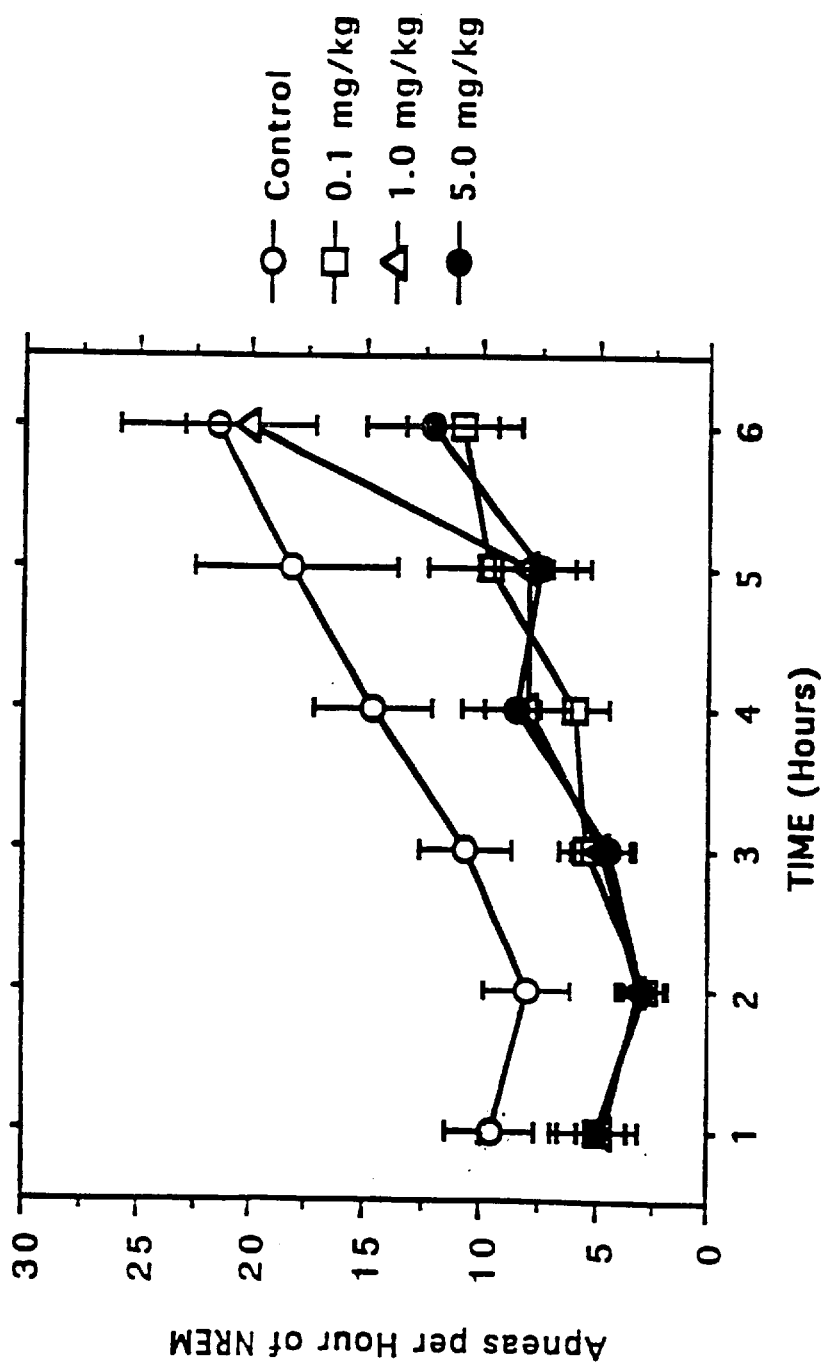
FIG. 6 shows the effects of serotonin (0.79 mg/kg), GR38032F (0.1 mg/kg)+serotonin (0.79 mg/kg), and GR38032F (0.1 mg/kg) on spontaneous apneas in NREM sleep. Each data bar represents the mean ± the standard error over 6 recording hours with all animals (n=10; p=0.97).

Results of the administration of either serotonin alone (0.79 mg/kg), GR38032F (0.1 mg/kg)+serotonin (0.79 mg/kg), or GR38032F alone (0.1 mg/kg) on the ability to promote spontaneous apneas in NREM sleep during a 6 hour polygraphic recording is set forth in FIG. 6. Specifically, during NREM sleep, the spontaneous apnea index was not affected by any drug treatment.

Figure 7:
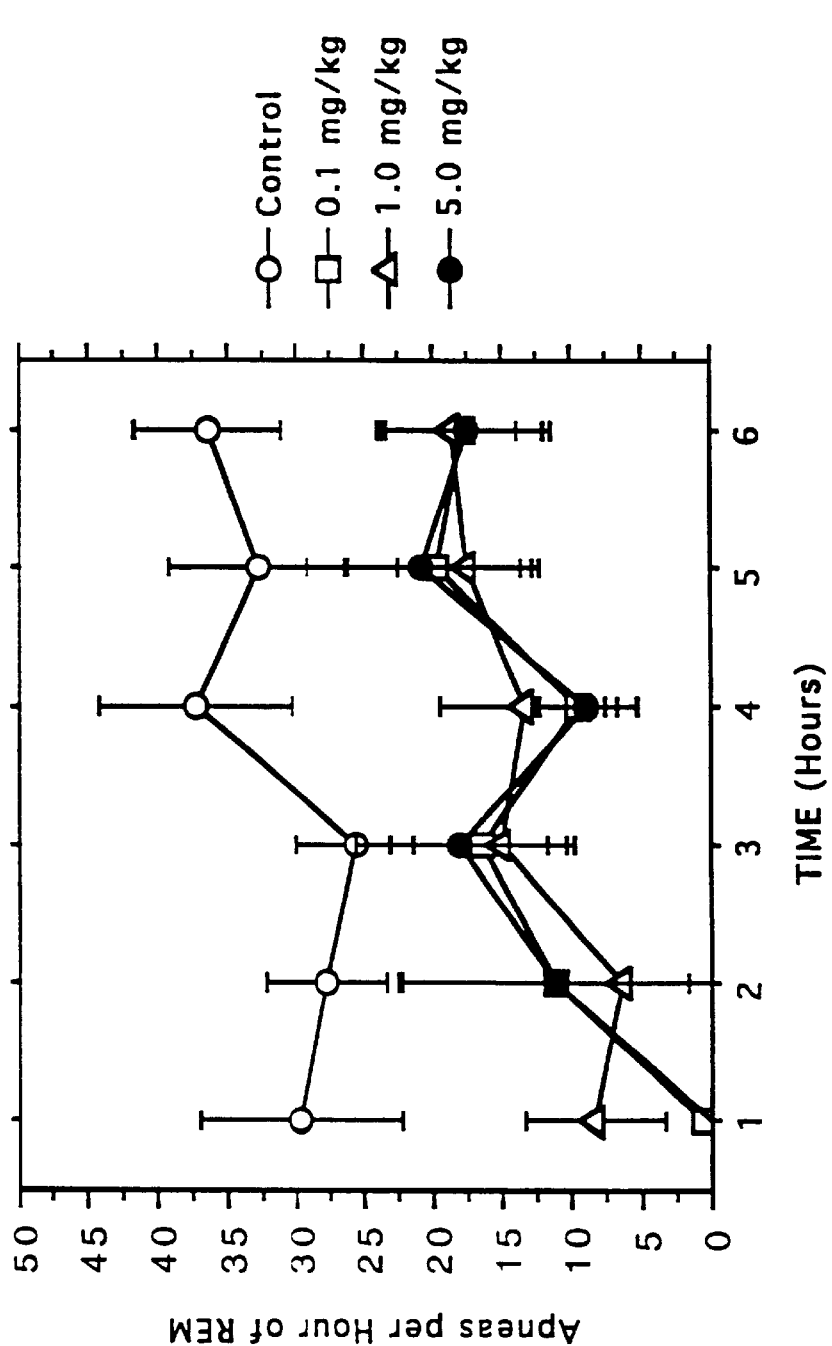
FIG. 7 illustrates the effects of serotonin (0.79 mg/kg), GR38032 (0.1 mg/kg)+serotonin (0.79 mg/kg), and GR38032F (0.1 mg/kg) on spontaneous apneas during REM sleep. Each data bar represents the mean ± the standard error over 6 recording hours with all animals (n=10; p=0.01 for serotonin administration vs. control; p=0.05 for administration of GR38032F+serotonin vs. serotonin alone; p=0.99 for administration of GR38032F+serotonin vs. control; and p=0.51 for administration of GR38032F alone).

As illustrated in FIG. 7, spontaneous apnea expression during REM sleep significantly increased following administration of serotonin as compared to control recording (>250% increase). Results also indicate that such an increase was abolished via prior administration of GR38032F. At the low dose tested (0.1 mg/kg) administration of GR38032F alone had no effect on REM sleep spontaneous apneas.

As set forth in Table 2 (percentages of waking, NREM, and REM sleep during 6 hours of polygraphic recording following drug administration), intraperitoneal administration of serotonin alone, GR38032F+serotonin, or GR38032F alone had no effect on sleep architecture. Finally, no treatment group tested had a significant effect on RR, VE, mean BP, HP, or PS apnea index (data not shown).

TABLE 2

Effects of 5-HT and GR38032F on Sleep/Wake Architecture

|  | % Wakefulness | % NREM | % REM |
| --- | --- | --- | --- |
| Control (saline solution) | 33.7 ± 2.5* | 58.0 ± 1.9 | 6.9 ± 1.1 |
| 5-HT (0.79 mg/kg) | 30.2 ± 3.2 | 59.9 ± 3.3 | 6.5 ± 1.1 |
| 5-HT + GR38032F | 36.7 ± 8.7 | 56.0 ± 7.6 | 5.3 ± 1.4 |
| GR38032F (0.1 mg/kg) | 28.8 ± 6.4 | 63.4 ± 5.7 | 7.3 ± 2.3 |
| p (1-way ANOVA) | 0.43 | 0.71 | 0.60 |

*All values reflect means ± SE for percent recording time.

Overall these results indicate that manipulation of peripheral serotonin receptors exerts a potent influence on the generation of central apneas during REM sleep. Specifically, the present results show that systemic administration of serotonin increases spontaneous apnea expression in sleep. Although the dose of serotonin employed had no effect on sleep, cardiovascular variables, RR, or VE, the REM-related spontaneous apnea index increased >250%. Further, it is important to note that the mechanisms of apnea genesis are at least partially sleep-state specific, as NREM apneas were unaffected.

These findings demonstrate that exogenous administration of 5-hydroxytryptamine$_3$ agonists and antagonists at various doses produces changes in apnea expression that are specific to REM sleep. Such findings indicate that there is a physiologic role for endogenous serotonergic activity in modulating the expression of apnea, especially during REM sleep. Moreover, because serotonin does not cross the blood-brain barrier, the finding that serotonin exerts a converse effect to GR38032F indicates that the relevant receptors are located in the peripheral nervous system. Further, the present data suggest that the action of supraphysiologic levels of serotonin on apneas is receptor mediated in that pretreatment with a low dose (0.1 mg/kg) of GR38032F, which had no independent effect on any measured parameter, including apneas, fully blocked the effects of exogenous serotonin on apnea expression.

In view of the foregoing data, the likely peripheral site of action for the observed apnea-promoting effects of serotonin administration is thought to be the nodose ganglia of the vagus nerve. More specifically, several studies have concluded that the apnea component of the Bezold-Jarisch reflex results from the action of serotonin at the nodose ganglia in cats [Jacobs et al., Circ. Res., 29:145–155 (1971), Sampson et al., Life Sci., 15:2157–2165 (1975), Sutton, Pflugers Arch., 389:181–187 (1981)] and rats [Yoshioka et al., J. Pharmacol. Exp. Ther., 260:917–924 (1992) and McQueen et al., J. Physiol, 5073:843–855 (1998)]. Intravenous administration of serotonin or 5-hydroxytryptamine$_3$ receptor agonists also stimulates pulmonary vagal receptors [McQueen et al., J. Physiol., 5073:843–855 (1998)], which may contribute significantly to the apneic response.

Although species differences may be present [Black et al., Am. J. Physiol., 223:1097–1102 (1972)], several studies in rat demonstrate that, in addition to its impact on vagal signaling, serotonin also elicits increased firing from carotid body chemoreceptors [McQueen et al., J. Physiol., 5073:843–855 (1998); Sapru et al., Res. Comm. Chem. Pathol. Phannacol., 16:245–250 (1977); Yoshioka, J. Pharmacol. Exp. Ther., 250:637–641 (1989) and Yoshioka et al., Res. Comm. Chem. Pathol. Pharmacol., 74:39–45 (1991)] and increased VE [McQueen et al., J. Physiol., 5073:843–855 (1998); Sapru et al., Res. Comm. Chem. Pathol. Pharmacol., 16:245–250 (1977)]. Although chemoreceptor-mediated effects on apnea cannot be ruled out, the data of McQueen et al., J. Physiol., 5073:843–855 (1998) strongly indicate that intravenous serotonin elicits apnea via a vagal pathway, while the chemoreceptor activation opposes apnea genesis in the anesthetized rat.

The serotonin-induced Bezold-Jarisch reflex in anesthetized animals includes apnea and bradycardia. At the dose employed, serotonin did not elicit changes in either heart rate or mean BP over the 6 hour recording period. Beat-to-beat heart rate and BP variability, assessed as coefficients of variation, were also unaffected by serotonin at the dose tested. The observed dissociation of cardiovascular and respiratory responses to serotonin indicates that changes in apnea expression were not baroreceptor mediated.

Although the Bezold-Jarisch reflex in anesthetized animals and serotonin-induced apneas in REM sleep are not the same phenomenon, they may be related by similar mechanisms. When serotonin receptors are strongly manipulated by exogenous means, i.e., either with serotonergic agonists or antagonists, the expression of spontaneous apneas in REM sleep can be amplified or suppressed. However, our observation that 1 mg/kg GR38032F significantly suppressed REM apneas does not preclude a role for 5-hydroxytryptamine$_2$ or other 5-hydroxytryptamine receptor subtypes in the peripheral regulation of the apnea expression, and infact the invention also contemplates the use of 5-hydroxytryptamine$_2$ and 5-hydroxytryptamine$_3$, alone or in combination as well as serotonin antagonists that exhibit both type 2 and type 3 receptor antagonism (see Example 4).

It has been well established [Mendelson et al., Physiol. Behav., 43:229–234 (1988); Sato et al., Am. J. Physiol., 259: R282–287 (1990); Monti et al., Pharmacol. Biochem. Behav., 51:125–131 (1995); Monti et al., Pharmacol. Biochem. Behav., 53:341–345 (1996); Thomas et al., J. Appl. Physiol., 73:1530–1536 (1992) and Thomas et al., J. Appl. Physiol., 78:215–218 (1995)] that apnea frequency in rats increases from deep slow-wave sleep to light NREM sleep to REM sleep, as is the case in man. The high incidence of apnea expression during REM sleep may be related to respiratory changes that take place during this sleep state. Typically, during REM sleep, breathing becomes shallow and irregular [Orem et al., Respir. Physiol., 30:265–289 (1977); Phillipson, Annu. Rev. Physiol., 40:133–156 (1978); Sieck et al., Exp. Neurol., 67:79–102 (1980) and Sullivan, In:Orems et al., eds., "Physiology in sleep," Academic Press, New York, N.Y., pp. 213–272 (1980)] and VE is at its lowest point [Hudgel et al., J. Appl. Phisyol., 56:133–137 (1984)]. This background of low respiratory output coupled with strong phasic changes in autonomic activity [Mancia et al., In; Orem et al., eds., "Physiology in sleep," Academic Press, New York, N.Y., pp. 1–55 (1980)] would render respiratory homeostasis during REM sleep more vulnerable to interruption by apnea. Thus it is possible that the role of serotonin activity in the peripheral nervous system in REM apnea genesis may arise from a serotonergic modulation of either tonic or phasic activity of respiratory afferent activity, especially in the vagus nerves. Therefore, the brainstem respiratory integrating areas may be rendered more vulnerable to fluctuating afferent inputs during REM sleep.

Overall, the results presented herein indicate that the exacerbation of spontaneous apnea during REM sleep produced by peripherally administered serotonin is receptor mediated. Such findings also indicate a physiologic role for endogenous serotonin in the peripheral nervous system in modulating sleep apnea expression under baseline conditions.

EXAMPLE 4

Suppression or Prevention of Sleep Apneas

As indicated by the data presented herein (see Examples 2 and 3) serotonin plays an important and integral role in apnea genesis, which is both highly site and receptor subtype specific. More specifically, the efficacy of a serotonin receptor antagonist to suppress apnea is based on its activity in the peripheral nervous system, with the nodose ganglia of the vagus nerves appearing to be a crucial target site. 5-hydroxytryptamine$_2$ and 5-hydroxytryptamine$_3$ receptors at this site are clearly implicated in serotonin-induced apnea in anesthetized animals [Yoshioka et al, *J. Pharmacol. Exp. Therp.*, 260:917–924 (1992)]. In conjunction with these previous findings, the data presented herein (that administration of serotonin strictly to the peripheral nervous system exacerbates sleep-related apnea) indicates the importance of nodose ganglion serotonin receptors of both types in sleep apnea pathogenesis. Moreover, the serotonin-induced increase in apnea expression was completely blocked by a low dose of GR38032F, a 5-hydroxytryptamine$_3$ antagonist. Such a result indicates that the previously demonstrated suppression of apnea by GR38032F (see Example 2) most probably resulted from activity in the peripheral nervous system.

Therefore, in view of the foregoing, sleep related breathing disorders (sleep apnea syndrome, apnea of infancy, Cheyne-Stokes respiration, sleep-related hypoventilation syndromes) may be effectively prevented or suppressed via systemic administration of pharmacological agents exhibiting either serotonin type 2 or type 3 receptor antagonism, alone or in combination as well as agents that exhibit both serotonin type 2 and type 3 receptor antagonism.

Effective treatments for the prevention or suppression of sleep-related breathing disorders include systemic administration of a 5-hydroxytryptamine$_2$ or 5-hydroxytryptamine$_3$ receptor antagonist either alone or in combination. In a preferred embodiment the serotonin receptor antagonist has activity only in the peripheral nervous system and/or does not cross the blood-brain barrier. In a more preferred embodiment the serotonin receptor antagonist displays both 5-hydroxytryptamine$_2$ and 5-hydroxytryptamine$_3$ receptor subtype antagonism.

Current pharmacological treatments for sleep-related breathing disorders also involve apnea suppression via serotonin agonist effects within the central nervous system, and more specifically the brainstem. Indeed, it was in view of their potential to stimulate respiration and upper airway motor outputs that serotonin enhancing drugs were originally tested as pharmacological treatments for sleep apnea syndrome. One early report suggested that L-tryptophan, a serotonin precursor, may have a beneficial effect on sleep apnea syndrome [Schmidt, *Bull. Eur. Physiol. Respir.*, 19:625–629 (1982)]. More recently fluoxetine [Hanzel et al., *Chest.*, 100:416–421 (1991)] and paroxetine [Kraiczi et al., *Sleep*, 22:61–67 (1999)], both selective serotonin reuptake inhibitors (SSRIs), were demonstrated to benefit some but not all patients with sleep apnea syndrome. In addition, combinations of serotonin precursors and reuptake inhibitors reduced sleep disordered respiration in English bulldog model of sleep apnea syndrome [Veasey et al., *Sleep Res.*, A529; 1997 and Veasey et al., *Am. J. Resp. Crit. Care Med.*, 157: A655 (1997)]. However, despite ongoing investigations these encouraging early results with serotonin enhancing drugs have not been reproduced.

The foregoing efforts with serotonin-enhancing drugs indicate that the potential utility of serotonin precursors or SSRIs in apnea treatment resides strictly in their central nervous system effects. Therefore, it is precisely because the serotonin enhancing effects of SSRIs in the peripheral nervous have been left unchecked that these compounds have not demonstrated reproducible effects in apnea treatment. In fact buspirone, a specific 5-hydroxytryptamine$_{1A}$ agonist, which stimulates respiration [Mendelson et al., *Am. Rev. Respir. Dis.*, 141:1527–1530 (1990)], has been shown to reduce apnea index in 4 of 5 patients with sleep apnea syndrome [Mendelson et al., *J. Clin. Psychopharmacol.*, 11:71–72 (1991)] and to eliminate post-surgical apneustic breathing in one child [Wilken et al., *J. Pediatr.*, 130:89–94 (1997). Although buspirone acts systemically, 5-hydroxytryptamine$_1$ receptors in the peripheral nervous system have not been shown to play a role in apnea genesis. The modest apnea suppression induced by buspirone is a central nervous system effect that goes unopposed by serotonergic effects in the peripheral nervous system.

The rationale for using SSRIs such as fluoxetine or paroxetine to treat sleep apnea syndrome rests in part on their ability to stimulate upper airway motor outputs. Applications of serotonin to the floor of the fourth ventricle [Rose et al., *Resp. Physiol.*, 101:59–69 (1995)] or into the hypoglossal motor nucleus [Kubin et al., *Neurosci. Lett.*, 139:243–248 (1992)] produce upper airway motor activation in cats; effects which appear to be mediated predominantly by 5-hydroxytryptamin$_2$ receptors. Conversely, systemic administration of 5-hydroxytryptamine$_2$ receptor antagonists to English bulldogs reduces electrical activation of upper airway muscles, diminishes upper airway cross-sectional area and promotes obstructive apnea [Veasey et al., *Am. J. Crit. Care Med.*, 153:776–786 (1996)]. These observations provide a likely explanation for the improvements in sleep-disordered breathing observed in some patients following SSRI treatment.

In conjunction with the data presented herein (Examples 2 and 3) and the foregoing observations, sleep related breathing disorders (sleep apnea syndrome, apnea of infancy, Cheyne-Stokes respiration, sleep-related hypoventilation syndromes) may be effectively prevented or suppressed via systemic administration of (a) an agent or combinations of agents exhibiting either serotonin type 2 or type 3 receptor antagonism (either alone or in combination with one another) and/or in combination with either a 5-hydroxytryptamine$_1$ or 5-hydroxytryptamine$_2$ receptor agonist;

(b) an agent or combination of agents or agents that exhibit both serotonin type 2 and type 3 receptor antagonism in combination with either a 5-hydroxytryptamine$_1$ or 5-hydroxytryptamine$_2$ receptor agonist; or (c) agents that exhibit both the proper antagonistic and agonistic pharmacological profile (i.e., an agent that is both an agonist and antagonist at the receptor subtypes set forth above).

Preferred embodiments include the following:
  (a) an agent or combination of agents wherein the serotonin agonist exhibits only central serotonergic actions;
  (b) an agent or combination of agents wherein the serotonin agonist exhibits only central 5-hydroxytryptamine$_2$ actions;
  (c) an agent or combination of agents s wherein the serotonin antagonist exhibits only peripheral actions while the serotonin agonist exhibits only central serotonergic actions;
  (d) an agent or combination of agents that have the ability to induce central nervous system serotonin release and that possess the antagonistic profile discussed above (i.e. both a 5-hydroxytryptamine$_2$ and 5-hydroxytryptamine$_3$ receptor antagonist); or
  (e) an agent or combination of agents that have the ability to induce central nervous system serotonin release and possess only peripheral antagonistic effects;

Those of skill in the art will recognize that many serotonin receptor agonists such as, but not limited to 8-OH-DPAT (8-hydroxy-2-(di-n-propylamino)tetralin, sumatriptan, L694247 (2-[5-[3-(4-methylsulphonylamino)benzyl-1,2,4-oxadiazol-5-yl]-1H-indol-3yl]ethanamine), buspirone, alnitidan, zalospirone, ipsapirone, gepirone, zolmitriptan, risatriptan, 311C90, α-Me-5-HT, BW723C86 (1-[5(2-thienylmethoxy)-1H-3-indolyl[propan-2-amine hydrochloride), MCPP (m-chlorophenylpiperazine), as well as others may be used in conjunction with serotonin receptor antagonists to prevent or ameliorate sleep-related breathing disorders.

Pharmacological mechanisms of action other than serotonin precursors or SSRIs may also be exploited to enhance central nervous system serotonin activity. Indeed, at least one mechanism allows augmented serotonin release to be selectively targeted at the central nervous system. Specifically, antagonism of presynaptic α$_2$ adrenergic receptors located on brainstem serotonergic neurons (heteroreceptors) enhances serotonin release. Selective 5-hydroxytryptamine$_2$ and 5-hydroxytryptamine$_3$ receptor antagonists have been shown to block presynaptic α$_2$-adrenoreceptors as well as postsynaptic 5-hydroxytryptamine$_2$ and 5-hydroxytryptamine$_3$ receptors [deBoer, *J. Clin. Psychiatr.*, 57(4):19–25 (19960; Devane, *J. Clin. Psychiatry.*, 59(20):85–93 (1998); and Puzantian, *Am. J. Heatlh-Syst. Phann.*, 55:44–49 (1998)]. Because the affinity of such agents for central α$_2$ receptors is 10 times higher than for peripheral α$_2$ receptors [Puzantian, *Am. J. Heatlh-Syst. Pharm.*, 55:44–49 (1998)], central serotonin release is increased with minimal adrenergic side effects such as hypertension. Thus because these pharmacological agents are high affinity antagonists at 5-hydroxytryptamine$_{2A}$, 5-hydroxytryptamine$_{2C}$, and 5-hydroxytryptamine$_3$ receptors, the net effect is increased post-synaptic 5-hydroxytryptamine$_1$ activity within the brain and reduced 5-hydroxytryptamine$_2$ and 5-hydroxytryptamine$_3$ post-synaptic activity in the central and peripheral nervous systems. Each of these pharmacological effects serve to stimulate respiration and suppress apnea.

In view of the foregoing observations, sleep related breathing disorders (sleep apnea syndrome, apnea of infancy, Cheyne-Stokes respiration, sleep-related hypoventilation syndromes) may also be effectively suppressed or prevented via systemic administration of pharmacological agents of combinations of agents having α$_2$ adrenergic antagonist activity with either serotonin type 2 or type 3 receptor antagonist activity (either alone or in combination with one another). Preferred embodiments include:
  (a) an agent or combination of agents wherein the α$_2$ adrenergic antagonist effects are exerted centrally;
  (b) an agent or combination of agents wherein the serotonin antagonist effects are exerted peripherally;
  (c) an agent or combination of agents wherein the α$_2$ adrenergic antagonist effects are exerted centrally and the serotonin antagonist effects are exerted peripherally;
  (d) the agent or combination of agents of embodiments a–c wherein the α$_2$ adrenergic antagonist effect is exerted presynaptically;
  (e) the agent or combination of agents of embodiments a–d wherein the α$_2$ adrenergic antagonist effects are exerted selectively at presynaptic heteroreceptors on serotonergic neurons; or
  (f) the agent or combination of agents of embodiments a–d in which the α$_2$ adrenergic antagonist effect is exerted by an agent or combination of agents possessing the following pharmacological profile: αa$_2$ adrenergic antagonist activity with both serotonin type 2 or type 3 receptor antagonist activity.

Those of skill in the art will recognize that many α$_2$ adrenergic receptor antagonists such as, but not limited to phenoxybenzamine, phentolamine, tolazoline, terazosine, doxazosin, trimazosin, yohimbine, indoramin, ARC239, prazosin as well as others may be used in conjunction with serotonin receptor antagonists to prevent or ameliorate sleep-related breathing disorders An individual diagnosed with a sleep-related breathing disorder is administered either a composition or agent having any of the foregoing pharmacological profiles in an amount effective to prevent or suppress such disorders. The specific dose may be calculated according to such factors as body weight or body surface. Further refinement of the calculations necessary to determine the appropriate dosage for treatment of sleep-related breathing disorders is routinely made by those of ordinary skill in the art without undue experimentation. Appropriate dosages may be ascertained through use of established assays for determining dosages. Routes of administration for the foregoing methods may be by any systemic means including oral, intraperitoneal, subcutaneous, intravenous, intramuscular, transdermal, or by other routes of administration. Osmotic mini-pumps and timed-released pellets or other depot forms of administration may also be used.

Finally, those of skill in the art will recognize that with respect to the compounds discussed above, such compounds may contain a center of chirality. Thus such agents may exist as different enantiomers of enantiomeric mixtures. Use of any one enantiomer alone or contained within an enantiomeric mixture with one or more stereoisomers is contemplated by the present invention.

Although the present invention has been described in terms of preferred embodiments, it is intended that the present invention encompass all modifications and variations that occur to those skilled in the art upon consideration of the disclosure herein, and in particular those embodiments that are within the broadest proper interpretation of the claims and their requirements. All literature cited herein is incorporated by reference.

What is claimed is:

1. A method of preventing or ameliorating sleep-related breathing disorder the method comprising administering to a patient in need thereof an effective amount of a serotonin receptor antagonist.

2. The method of claim 1 wherein the sleep-related breathing disorder is selected from the group consisting of obstructive sleep apnea syndrome, apnea of prematurity, congenital central hypoventilation syndrome, obesity hypoventilation syndrome, central sleep apnea syndrome, Cheyne-Stokes respiration, and snoring.

3. The method of claim 1 or claim 2 wherein the serotonin receptor antagonist is selected from the group consisting of ketanserin, cinanserin, LY-53,857, metergoline, LY-278,584, methiothepin, p-NPPL, NAN-190, piperazine, SB-206553, SDZ-205,557, 3-tropanyl-indole-3-carboxylate, 3-tropanyl-indole-3-carboxylate methiodide, methysergide, risperidone, cyproheptadine, clozapine, mianserin, ritanserin, and granisetron.

4. The method of claim 1 or claim 2 wherein the serotonin receptor antagonist is a 5-hydroxytryptamine$_2$ receptor subtype antagonist.

5. The method of claim 1 or claim 2 wherein the serotonin receptor antagonist is a 5-hydroxytryptamine$_3$ receptor subtype antagonist.

6. The method of claim 1 or claim 2 wherein the serotonin receptor antagonist is both a 5-hydroxytryptamine$_2$ receptor subtype antagonist and a 5-hydroxytryptamine$_3$ receptor subtype antagonist.

7. A method of preventing or ameliorating sleep-related breathing disorders the method comprising administering to a patient in need thereof an effective amount of an agent or combination of agents having both 5-hydroxytryptamine$_2$ subtype receptor antagonistic activity and 5-hydroxytryptamine$_3$ subtype receptor antagonistic activity.

8. The method of claim 7 wherein the sleep-related breathing disorder is selected from the group consisting of obstructive sleep apnea syndrome, apnea of prematurity, congenital central hypoventilation syndrome, obesity hypoventilation syndrome, central sleep apnea syndrome, Cheyne-Stokes respiration, and snoring.

9. The method of claim 7 or claim 8 wherein the effects of the agent or combination of agents are exerted only in the peripheral nervous system.

10. A method of preventing or ameliorating sleep-related breathing disorders the method comprising administering to a patient in need thereof an effective amount of a composition comprising a serotonin receptor antagonist and a serotonin receptor agonist.

11. The method of claim 10 wherein the sleep-related breathing disorder is selected from the group consisting of obstructive sleep apnea syndrome, apnea of prematurity, congenital central hypoventilation syndrome, obesity hypoventilation syndrome, central sleep apnea syndrome, Cheyne-Stokes respiration, and snoring.

12. The method of claim 10 or claim 11 wherein the serotonin receptor antagonist is selected from the group consisting of ketanserin, cinanserin, LY-53,857, metergolne, LY-278,584, methiothepin, p-NPPL, NAN-190, piperazine, SB-206553, SDZ-205,557, 3-tropanyl-indole-3-carboxylate, 3-tropanyl-indole-3-carboxylate methiodide, methysergide, risperidone, cyproheptadine, clozapine, mianserin, ritanserin, and granisetron.

13. The method of claim 10 or claim 11 wherein the serotonin receptor agonist is selected from the group consisting of 8-OH-DPAT, sumatriptan, L694247, buspirone, alnitidan, zalospirone, ipsapirone, gepirone, zolmitriptan, risatriptan, 311C90, α-Me-5-HT, BW723C86, and MCPP.

14. The method of claim 10 or claim 11 wherein the serotonin receptor antagonist is a 5-hydroxytryptamine$_2$ receptor subtype antagonist.

15. The method of claim 10 or claim 11 wherein the serotonin receptor antagonist is a 5-hydroxytryptamine$_3$ receptor subtype antagonist.

16. The method of claim 10 or claim 11 wherein the serotonin receptor agonist is a 5-hydroxytryptamine$_1$ receptor subtype agonist.

17. The method of claim 10 or claim 11 wherein the serotonin receptor agonist is a 5-hydroxytryptamine$_2$ receptor subtype agonist.

18. The method of claim 10 or claim 11 wherein the effects of the serotonin receptor agonist are exerted in the central nervous system.

19. The method of claim 10 or claim 11 wherein the effects of the serotonin receptor antagonist are exerted in the peripheral nervous system.

20. The method of claim 10 or claim 11 wherein the effects of the serotonin receptor agonist are exerted in the central nervous system and wherein the effects of the serotonin receptor antagonist are exerted in the peripheral nervous system.

21. The method of claim 10 or claim 11 wherein the serotonin receptor antagonist exhibits both 5-hydroxytryptamine$_2$ and 5-hydroxytryptamine$_3$ receptor subtype antagonistic activity.

22. A method of preventing or ameliorating sleep-related breathing disorders the method comprising administering to a patient in need thereof an effective amount of an agent or combination of agents exhibiting both 5-hydroxytryptamine$_2$ and 5-hydroxytryptamine$_3$ receptor subtype antagonistic activity and wherein the agent or combination of agents further exhibits the ability to induce serotonin release within the central nervous system.

23. The method of claim 22 wherein the sleep-related breathing disorder is selected from the group consisting of obstructive sleep apnea syndrome, apnea of prematurity, congenital central hypoventilation syndrome, obesity hypoventilation syndrome, central sleep apnea syndrome, Cheyne-Stokes respiration, and snoring.

24. The method of claim 21 or claim 22 wherein the agent or combination of agents demonstrate the serotonin receptor antagonistic activity only in the peripheral nervous system.

25. A method of preventing or ameliorating sleep-related breathing disorders the method comprising administering to a patient in need thereof an effective amount of an agent or composition exhibiting $\alpha_2$ adrenergic receptor subtype antagonism and either 5-hydroxytryptamine$_2$ or 5-hydroxytryptamine$_3$ receptor subtype antagonism or both.

26. The method of claim 25 wherein the sleep-related breathing disorder is selected from the group consisting of obstructive sleep apnea syndrome, apnea of prematurity, congenital central hypoventilation syndrome, obesity hypoventilation syndrome, central sleep apnea syndrome, Cheyne-Stokes respiration, and snoring.

27. The method of claim 25 or claim 26 wherein the serotonin receptor antagonist is selected from the group consisting of ketanserin, cinanserin, LY-53,857, metergoline, LY-278,584, methiothepin, p-NPPL, NAN-190, piperazine, SB-206553, SDZ-205,557, 3-tropanyl-indole-3-carboxylate, 3-tropanyl-indole-3-carboxylate methiodide, methysergide, risperidone, cyproheptadine, clozapine, mianserin, ritanserin, and granisetron.

28. The method of claim 25 or claim 26 wherein the $\alpha_2$ adrenergic receptor subtype antagonist is selected from the group consisting of phenoxybenzamine, phentolamine, tolazoline, terazosine, doxazosin, trimazosin, yohimbine, indoramin, ARC239, and prazosin.

29. The method of claim 25 or claim 26 wherein the $\alpha_2$ adrenergic antagonist effects are exerted within the central nervous system.

30. The method of claim 25 or claim 26 wherein the serotonin antagonist effects are exerted in the peripheral nervous system.

31. The method of claim 25 or claim 26 wherein the $\alpha_2$ adrenergic antagonist effects are exerted in the central nervous system and the serotonin antagonist effects are exerted in the peripheral nervous system.

32. The method of claim 29 wherein the $\alpha_2$ adrenergic antagonist effect is exerted presynaptically.

33. The method of claim 30 wherein the $\alpha_2$ adrenergic antagonist effect is exerted presynaptically.

34. The method of claim 31 wherein the $\alpha_2$ adrenergic antagonist effect is exerted presynaptically.

35. The method of claim 29 wherein the $\alpha_2$ adrenergic antagonist effects are exerted selectively at presynaptic heteroreceptors located on serotonergic neurons.

36. The method of claim 30 wherein the wherein the $\alpha_2$ adrenergic antagonist effects are exerted selectively at presynaptic heteroreceptors located on serotonergic neurons.

37. The method of claim 31 wherein the wherein the $\alpha_2$ adrenergic antagonist effects are exerted selectively at presynaptic heteroreceptors located on serotonergic neurons.

* * * * *

UNITED STATES PATENT AND TRADEMARK OFFICE
CERTIFICATE OF CORRECTION

PATENT NO. : 6,331,536 B1
DATED : December 18, 2001
INVENTOR(S) : Miodrag Radulovacki et al.

It is certified that error appears in the above-identified patent and that said Letters Patent is hereby corrected as shown below:

Title page,
Item [56], OTHER PUBLICATIONS,
Author Butler: "Anatagonist" should be -- Antagonist --
Author Hilaire et al.: "Changes in Serotoniin Metabloism May Elicit Obstructive Apnoea ib the Newnborn Rat" should be -- Changes in Serotonin Metabolism May Elicit Obstructive Apnoea in the Newborn Rat --
Author Kubin: "Montoneurons" should be -- Motoneurons --
Author Sapru et al: "thr" should be -- the --

Column 5,
Line 38, delete the space between "trim" and azosin"

Column 6,
Line 27, "Pharnacodyn" should be -- Pharmacodyn --
Line 46, "2-methylirnidazol" should be -- 2-methylimidazol --

Column 8,
Line 36, "Denial" should be -- Dental --

Column 9,
Line 67, "GR30832F" should be -- GR38032F --

Column 15,
Line 24, "Phannacol" should be -- Pharmacol --

Column 17,
Line 7, delete "s" between "agents" and "wherein"

Column 18,
Line 19, "αa2" should be -- $\alpha_2$ --

Column 19,
Line 51, "metergolne" should be replaced with -- metergoline -- in claim 12.

UNITED STATES PATENT AND TRADEMARK OFFICE
CERTIFICATE OF CORRECTION

PATENT NO.   : 6,331,536 B1
DATED        : December 18, 2001
INVENTOR(S)  : Miodrag Radulovacki et al.

It is certified that error appears in the above-identified patent and that said Letters Patent is hereby corrected as shown below:

Column 22,
Line 4, delete the second occurrence of "wherein the" in claim 36.
Line 7, delete the second occurrence of "wherein the" in claim 37.

Signed and Sealed this

Tenth Day of December, 2002

JAMES E. ROGAN
*Director of the United States Patent and Trademark Office*

UNITED STATES PATENT AND TRADEMARK OFFICE
Certificate

Patent No. 6,331,536 B1                                               Patented: December 18, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Miodrag Radulovacki, Chicago, IL (US); David W. Carley, Evanston, IL (US); and John Stuart Andrews, Missussauga, Ontario, Canada.

Signed and Sealed this Seventeenth Day of June 2008.

ARDIN MARSCHEL
*Supervisory Patent Examiner*
Art Unit 1614